US012702820B2

(12) United States Patent
Pruvost et al.

(10) Patent No.: US 12,702,820 B2
(45) Date of Patent: Aug. 11, 2026

(54) SYSTEMS AND METHODS FOR POWERING AND CONTROLLING AN IMPLANTABLE HEART PUMP

(71) Applicant: CorWave SA, Clichy (FR)

(72) Inventors: Remi Pruvost, Reims (FR); Charlotte Rasser, Houilles (FR); Trevor Snyder, Fourqueux (FR); Yann Rigoudy, Cuvat (FR); Salome Chague, Clichy (FR)

(73) Assignee: CorWave SA, Clichy (FR)

(*) Notice: Subject to any disclaimer, the term of this patent is extended or adjusted under 35 U.S.C. 154(b) by 0 days.

(21) Appl. No.: 19/169,841

(22) Filed: Apr. 3, 2025

(65) Prior Publication Data

US 2025/0312588 A1 Oct. 9, 2025

Related U.S. Application Data

(60) Provisional application No. 63/631,334, filed on Apr. 8, 2024.

(30) Foreign Application Priority Data

Apr. 8, 2024 (EP) .................................... 24315131

(51) Int. Cl.
*A61M 60/508* (2021.01)
*A61M 60/178* (2021.01)
(Continued)

(52) U.S. Cl.
CPC ........ *A61M 60/508* (2021.01); *A61M 60/178* (2021.01); *A61M 60/585* (2021.01);
(Continued)

(58) Field of Classification Search
CPC .. A61M 60/122; A61M 60/508; A61M 60/81; A61M 60/871; A61M 60/878;
(Continued)

(56) References Cited

U.S. PATENT DOCUMENTS

| | | | |
|---|---|---|---|
| 2,842,067 | A | 7/1958 | John et al. |
| 3,107,630 | A | 10/1963 | Johnson et al. |

(Continued)

FOREIGN PATENT DOCUMENTS

| | | | |
|---|---|---|---|
| AU | 2013203301 | A1 | 5/2013 |
| AU | 2013302455 | A1 | 2/2015 |

(Continued)

OTHER PUBLICATIONS

International Search Report & Written Opinion dated Jun. 30, 2025 in Int'l PCT Patent Appl. Serial No. PCT/IB2025/053546 (141001).

(Continued)

*Primary Examiner* — Pamela M. Bays
(74) *Attorney, Agent, or Firm* — Greenberg Traurig, LLP; Christopher C. Bolten; Robert D. Ward

(57) ABSTRACT

Systems and methods for powering and controlling implantable heart pumps are provided. An example system may include an external controller housing for housing a processor programmable to control an implantable heart pump, a battery housing removably attachable to the external controller housing for housing battery cells to supply power to the implantable heart pump, a button connected to the battery housing, and a latch extending from the button to a latch protrusion. The button may be biased away from the battery housing in a locked position. In the locked position, the latch protrusion may engage with a latch receiver of the external controller housing to lock the external controller housing to the battery housing. The button may be depressed toward the battery housing to cause the latch protrusion to disengage from the latch receiver to permit the battery housing to be detached and removed from the external controller housing.

20 Claims, 14 Drawing Sheets

(51) Int. Cl.
*A61M 60/585* (2021.01)
*A61M 60/871* (2021.01)
*A61M 60/122* (2021.01)
*A61M 60/878* (2021.01)
*A61M 60/88* (2021.01)

(52) U.S. Cl.
CPC ......... *A61M 60/871* (2021.01); *A61M 60/122* (2021.01); *A61M 60/878* (2021.01); *A61M 60/88* (2021.01); *A61M 2205/04* (2013.01); *A61M 2205/82* (2013.01)

(58) Field of Classification Search
CPC .. A61M 60/88; A61M 60/585; A61M 60/178; A61M 2205/04; A61M 2205/82
See application file for complete search history.

(56) References Cited

U.S. PATENT DOCUMENTS 3,165,061 A 1/1965 Smith et al.
3,608,088 A 9/1971 Dorman et al.
3,620,651 A 11/1971 Peter
3,743,446 A 7/1973 Mandroian
3,765,175 A 10/1973 Ohnaka
4,063,826 A 12/1977 Riepe
4,164,046 A 8/1979 Cooley
4,277,706 A 7/1981 Isaacson
4,384,830 A 5/1983 Wakelin
4,484,095 A 11/1984 Neumann
4,488,854 A 12/1984 Miller
4,498,851 A 2/1985 Kolm et al.
4,648,807 A 3/1987 Tippetts et al.
4,753,221 A 6/1988 Kensey et al.
4,906,229 A 3/1990 Wampler
4,918,383 A 4/1990 Huff et al.
4,931,036 A 6/1990 Kanai et al.
4,939,405 A 7/1990 Okuyama et al.
4,955,856 A 9/1990 Phillips
4,995,857 A 2/1991 Arnold
5,147,388 A 9/1992 Yamazaki
5,263,978 A 11/1993 Kaufmann et al.
5,275,580 A 1/1994 Yamazaki
5,300,111 A 4/1994 Panton et al.
5,360,445 A 11/1994 Goldowsky
5,370,509 A 12/1994 Golding et al.
5,525,041 A 6/1996 Deak
5,588,812 A 12/1996 Taylor et al.
5,840,070 A 11/1998 Wampler
5,924,975 A 7/1999 Goldowsky
5,982,801 A 11/1999 Deak
6,030,336 A 2/2000 Franchi
6,058,593 A 5/2000 Siess
6,079,214 A 6/2000 Bishop
6,083,260 A 7/2000 Aboul-Hosn
6,116,862 A 9/2000 Rau et al.
6,123,725 A 9/2000 Aboul-Hosn
6,176,822 B1 1/2001 Nix et al.
6,176,848 B1 1/2001 Rau et al.
6,346,071 B1 2/2002 Mussivand
6,361,284 B2 3/2002 Drevet
6,395,026 B1 5/2002 Aboul-Hosn et al.
6,530,876 B1 3/2003 Spence
6,532,964 B2 3/2003 Aboul-Hosn et al.
6,658,740 B2 12/2003 Habben
6,659,740 B2 12/2003 Drevet
6,672,847 B2 1/2004 Dooley
6,723,039 B2 4/2004 French et al.
6,726,648 B2 4/2004 Kaplon et al.
6,732,501 B2 5/2004 Yu et al.
6,811,381 B2 11/2004 Dooley
6,848,001 B1 1/2005 Sakamoto et al.
6,935,344 B1 8/2005 Aboul-Hosn et al.
6,976,996 B1 12/2005 Aboul-Hosn
7,011,620 B1 3/2006 Siess
7,027,875 B2 4/2006 Siess et al.
7,182,727 B2 2/2007 Aboul-Hosn
7,323,961 B2 1/2008 Drevet
7,520,850 B2 4/2009 Brockway
7,696,634 B2 4/2010 Filardo
7,736,296 B2 6/2010 Siess et al.
7,839,007 B2 11/2010 Filardo
7,863,768 B2 1/2011 Filardo
7,889,877 B2 2/2011 Lutz
7,988,728 B2 8/2011 Ayre
8,012,079 B2 9/2011 Delgado, III
8,152,845 B2 4/2012 Bourque
8,157,720 B2 4/2012 Marseille et al.
8,167,593 B2 5/2012 Gohean et al.
8,333,686 B2 12/2012 Marseille et al.
8,343,029 B2 1/2013 Farnan et al.
8,366,401 B2 2/2013 Pate et al.
8,394,009 B2 3/2013 Bolyard et al.
8,394,010 B2 3/2013 Farnan
8,432,057 B2 4/2013 Filardo
8,449,444 B2 5/2013 Poirier
8,465,410 B2 6/2013 Marseille et al.
8,512,012 B2 8/2013 Akdis et al.
8,550,975 B2 10/2013 Foster
8,556,795 B2 10/2013 Bolyard et al.
8,562,508 B2 10/2013 Dague et al.
8,585,571 B2 11/2013 Bachman et al.
8,597,350 B2 12/2013 Rudser et al.
8,610,304 B2 12/2013 Filardo
8,714,944 B2 5/2014 Drevet
8,753,256 B2 6/2014 Bolyard et al.
8,784,291 B2 7/2014 Farnan et al.
8,821,366 B2 9/2014 Farnan et al.
8,821,527 B2 9/2014 Farnan et al.
8,827,888 B2 9/2014 Bolyard et al.
8,834,136 B2 9/2014 Drevet
8,852,072 B2 10/2014 LaRose et al.
8,870,739 B2 10/2014 LaRose et al.
8,956,275 B2 2/2015 Bolyard et al.
8,976,546 B2 3/2015 Wang et al.
9,022,916 B2 5/2015 Farnan et al.
9,080,564 B2 7/2015 Drevet
9,089,635 B2 7/2015 Reichenbach et al.
9,144,669 B2 9/2015 Wieselthaler
9,145,875 B2 9/2015 Filardo
9,173,984 B2 11/2015 LaRose et al.
9,211,367 B2 12/2015 Farnan et al.
9,308,304 B2 4/2016 Peters et al.
9,446,180 B2 9/2016 Vadala, Jr. et al.
9,526,819 B2 12/2016 Chen
9,572,915 B2 2/2017 Heuring et al.
9,579,437 B2 2/2017 LaRose et al.
9,616,158 B2 4/2017 Yaghdjian
9,694,123 B2 7/2017 Bourque et al.
9,731,057 B2 8/2017 Garrigue
9,744,279 B2 8/2017 Tamez et al.
9,786,150 B2 10/2017 Kimball et al.
9,861,728 B2 1/2018 Farnan et al.
9,907,892 B2 * 3/2018 Broen ................ A61M 60/508
9,956,333 B2 5/2018 LaRose et al.
9,968,720 B2 5/2018 Botterbusch et al.
9,976,546 B2 5/2018 Ishii et al.
9,981,076 B2 5/2018 Callaway et al.
10,166,319 B2 1/2019 Botterbusch et al.
10,188,779 B1 1/2019 Polverelli et al.
10,398,821 B2 9/2019 Botterbusch et al.
10,799,625 B2 10/2020 Scheffler et al.
10,823,164 B2 11/2020 Sauer
10,933,181 B2 3/2021 Le Duc De Lillers et al.
11,097,091 B2 8/2021 Botterbusch et al.
11,191,946 B2 12/2021 Snyder et al.
11,298,522 B2 4/2022 Botterbusch et al.
11,369,785 B2 6/2022 Callaway et al.
11,446,480 B2 9/2022 Polverelli et al.
11,512,689 B2 11/2022 Drevet et al.
11,623,077 B2 4/2023 Le Duc De Lillers et al.
11,712,554 B2 8/2023 Botterbusch et al.
12,005,245 B2 6/2024 Botterbusch et al.
12,017,059 B2 6/2024 Snyder et al.

(56) References Cited

U.S. PATENT DOCUMENTS

| | | | |
|---|---|---|---|
| 12,214,182 | B2 | 2/2025 | Polverelli et al. |
| 12,251,550 | B2 | 3/2025 | Quelenn et al. |
| 12,257,427 | B2 | 3/2025 | Snyder et al. |
| 12,453,847 | B2 | 10/2025 | Scheffler et al. |
| 12,485,268 | B2 | 12/2025 | Le Duc De Lillers et al. |
| 2001/0001278 | A1 | 5/2001 | Drevet |
| 2002/0095210 | A1 | 7/2002 | Finnegan et al. |
| 2002/0146333 | A1 | 10/2002 | Drevet |
| 2002/0165426 | A1 | 11/2002 | Sporer et al. |
| 2003/0002325 | A1 | 1/2003 | Alvandpour et al. |
| 2004/0002624 | A1 | 1/2004 | Yu et al. |
| 2004/0068220 | A1 | 4/2004 | Couvillon et al. |
| 2004/0152944 | A1 | 8/2004 | Medvedev et al. |
| 2005/0031474 | A1 | 2/2005 | Zackl |
| 2005/0261543 | A1 | 11/2005 | Abe et al. |
| 2005/0288543 | A1 | 12/2005 | Stenberg et al. |
| 2006/0014999 | A1 | 1/2006 | Heilman et al. |
| 2006/0155158 | A1 | 7/2006 | Aboul-Hosn |
| 2006/0288543 | A1 | 12/2006 | Lubera et al. |
| 2007/0197854 | A1 | 8/2007 | Marseille et al. |
| 2007/0299297 | A1 | 12/2007 | Jarvik |
| 2008/0232987 | A1 | 9/2008 | Drevet |
| 2009/0064755 | A1 | 3/2009 | Fleischli et al. |
| 2009/0082778 | A1 | 3/2009 | Beane et al. |
| 2010/0234941 | A1 | 9/2010 | Finocchiaro et al. |
| 2010/0241223 | A1 | 9/2010 | Lee et al. |
| 2010/0268333 | A1 | 10/2010 | Gohean et al. |
| 2011/0118833 | A1 | 5/2011 | Reichenbach et al. |
| 2011/0124950 | A1 | 5/2011 | Foster |
| 2011/0176945 | A1 | 7/2011 | Drevet |
| 2011/0176946 | A1 | 7/2011 | Drevet |
| 2011/0218385 | A1* | 9/2011 | Bolyard ............... A61M 60/411 600/16 |
| 2011/0238172 | A1 | 9/2011 | Akdis |
| 2011/0260449 | A1 | 10/2011 | Pokorney |
| 2011/0280755 | A1 | 11/2011 | Wackerle et al. |
| 2011/0313238 | A1 | 12/2011 | Reichenbach et al. |
| 2012/0035411 | A1 | 2/2012 | Larose et al. |
| 2012/0078030 | A1 | 3/2012 | Bourque |
| 2012/0089225 | A1 | 4/2012 | Akkerman et al. |
| 2012/0130153 | A1 | 5/2012 | Bolyard et al. |
| 2012/0177506 | A1 | 7/2012 | Örter |
| 2012/0220816 | A1 | 8/2012 | Peters et al. |
| 2012/0226350 | A1* | 9/2012 | Rudser ................ A61M 60/178 623/3.27 |
| 2012/0323318 | A1 | 12/2012 | Yusuf et al. |
| 2013/0042753 | A1 | 2/2013 | Becker et al. |
| 2013/0078122 | A1 | 3/2013 | Drevet |
| 2013/0178694 | A1 | 7/2013 | Jeffery et al. |
| 2013/0267779 | A1 | 10/2013 | Woolford et al. |
| 2013/0314047 | A1 | 11/2013 | Eagle et al. |
| 2014/0023533 | A1 | 1/2014 | Ishii et al. |
| 2014/0067057 | A1 | 3/2014 | Callaway et al. |
| 2014/0187852 | A1 | 7/2014 | Peters et al. |
| 2014/0207232 | A1 | 7/2014 | Garrigue |
| 2014/0275723 | A1 | 9/2014 | Fritz, IV et al. |
| 2014/0277423 | A1 | 9/2014 | Alkhatib et al. |
| 2014/0303426 | A1 | 10/2014 | Kerkhoffs et al. |
| 2014/0316426 | A1 | 10/2014 | Gollner et al. |
| 2014/0323796 | A1 | 10/2014 | Medvedev et al. |
| 2015/0031937 | A1 | 1/2015 | Kearsley et al. |
| 2015/0054336 | A1* | 2/2015 | Xinfang .................. F02N 11/12 307/9.1 |
| 2015/0167659 | A1 | 6/2015 | Sauer |
| 2015/0273124 | A1 | 10/2015 | Callaway et al. |
| 2015/0330383 | A1 | 11/2015 | Letailleur et al. |
| 2015/0374906 | A1 | 12/2015 | Forsell |
| 2016/0038664 | A1 | 2/2016 | Callaway et al. |
| 2016/0051738 | A1 | 2/2016 | Callaway et al. |
| 2016/0228628 | A1 | 8/2016 | Medvedev et al. |
| 2016/0235899 | A1 | 8/2016 | Yu et al. |
| 2016/0243294 | A1 | 8/2016 | Peters et al. |
| 2016/0258430 | A1 | 9/2016 | Merlen et al. |
| 2017/0000934 | A1 | 1/2017 | Miyakoshi |
| 2017/0012491 | A1 | 1/2017 | Schob et al. |
| 2017/0239407 | A1 | 8/2017 | Hayward |
| 2017/0266358 | A1 | 9/2017 | Aber |
| 2017/0290966 | A1 | 10/2017 | Botterbusch et al. |
| 2017/0290967 | A1 | 10/2017 | Botterbusch et al. |
| 2017/0296723 | A1 | 10/2017 | Garrigue |
| 2018/0038364 | A1 | 2/2018 | Dumas et al. |
| 2018/0050143 | A1 | 2/2018 | Nguyen et al. |
| 2018/0200422 | A1 | 7/2018 | Nguyen et al. |
| 2018/0243488 | A1 | 8/2018 | Callaway et al. |
| 2018/0250459 | A1 | 9/2018 | Kimball et al. |
| 2018/0256798 | A1 | 9/2018 | Botterbusch et al. |
| 2018/0369469 | A1 | 12/2018 | Le Duc De Lillers et al. |
| 2019/0001036 | A1 | 1/2019 | Casas et al. |
| 2019/0125949 | A1 | 5/2019 | Botterbusch et al. |
| 2019/0184082 | A1 | 6/2019 | Wolman et al. |
| 2019/0268332 | A1 | 8/2019 | Wang |
| 2019/0307938 | A1 | 10/2019 | Reyes et al. |
| 2019/0358383 | A1 | 11/2019 | Reyes et al. |
| 2019/0381227 | A1 | 12/2019 | Botterbusch et al. |
| 2020/0368417 | A1 | 11/2020 | Polverelli et al. |
| 2021/0015609 | A1 | 1/2021 | Dumontelle et al. |
| 2021/0085845 | A1 | 3/2021 | West |
| 2021/0093762 | A1 | 4/2021 | Chorpenning et al. |
| 2021/0121677 | A1 | 4/2021 | Nguyen et al. |
| 2021/0154384 | A1 | 5/2021 | Reyes et al. |
| 2021/0170160 | A1 | 6/2021 | Le Duc De Lillers et al. |
| 2021/0172429 | A1 | 6/2021 | Drevet et al. |
| 2021/0275797 | A1 | 9/2021 | Snyder et al. |
| 2021/0330960 | A1 | 10/2021 | Hall et al. |
| 2021/0361930 | A1 | 11/2021 | Johnson |
| 2021/0379353 | A1 | 12/2021 | Botterbusch et al. |
| 2021/0379361 | A1 | 12/2021 | Ramos et al. |
| 2022/0016412 | A1 | 1/2022 | Bourquin et al. |
| 2022/0203083 | A1 | 6/2022 | Wolman et al. |
| 2022/0296876 | A1 | 9/2022 | Callaway et al. |

FOREIGN PATENT DOCUMENTS

| | | | |
|---|---|---|---|
| AU | 2013203301 | B2 | 10/2015 |
| CA | 2712945 | A1 | 7/2009 |
| CN | 1257006 | A | 6/2000 |
| CN | 1355715 | A | 6/2002 |
| CN | 1714759 | A | 1/2006 |
| CN | 101472627 | A | 7/2009 |
| CN | 101878049 | A | 11/2010 |
| CN | 102112744 | A | 6/2011 |
| CN | 102284092 | A | 12/2011 |
| CN | 106421939 | A | 2/2017 |
| CN | 106489026 | A | 3/2017 |
| CN | 107635602 | A | 1/2018 |
| CN | 108514661 | A | 9/2018 |
| CN | 114367029 | A | 4/2022 |
| CN | 114470512 | A | 5/2022 |
| EP | 0412856 | A1 | 2/1991 |
| EP | 0415949 | A1 | 3/1991 |
| EP | 0412856 | B1 | 1/1994 |
| EP | 0445782 | B1 | 8/1994 |
| EP | 0925081 | B1 | 12/2003 |
| EP | 0961621 | B1 | 7/2004 |
| EP | 1551500 | A2 | 7/2005 |
| EP | 1233797 | B1 | 7/2006 |
| EP | 1337288 | B1 | 3/2008 |
| EP | 1981585 | A2 | 10/2008 |
| EP | 1644639 | B1 | 2/2009 |
| EP | 2152339 | A1 | 2/2010 |
| EP | 2249746 | A1 | 11/2010 |
| EP | 2310067 | A1 | 4/2011 |
| EP | 2600918 | A1 | 6/2013 |
| EP | 2517739 | B1 | 12/2013 |
| EP | 2704761 | A1 | 3/2014 |
| EP | 2310067 | B1 | 4/2014 |
| EP | 2753389 | A1 | 7/2014 |
| EP | 2152339 | B1 | 5/2015 |
| EP | 2891502 | A1 | 7/2015 |
| EP | 2704761 | B1 | 9/2015 |
| EP | 2736552 | B1 | 9/2015 |
| EP | 2891502 | B1 | 7/2016 |
| EP | 2164542 | B1 | 8/2016 |
| EP | 2856190 | B1 | 9/2016 |

(56) References Cited

FOREIGN PATENT DOCUMENTS

| | | | |
|---|---|---|---|
| EP | 3141269 | A1 | 3/2017 |
| EP | 3145558 | A2 | 3/2017 |
| ES | 2587072 | A1 | 10/2016 |
| FR | 355700 | A | 11/1905 |
| FR | 2650862 | B1 | 11/1991 |
| FR | 2744769 | A1 | 8/1997 |
| FR | 2744769 | B1 | 2/1999 |
| FR | 2861910 | B1 | 1/2006 |
| FR | 2905147 | A1 | 2/2008 |
| FR | 3032917 | A1 | 8/2016 |
| GB | 662047 | A | 11/1951 |
| JP | 2011509801 | A | 3/2011 |
| KR | 20130068373 | A | 6/2013 |
| WO | WO-8910763 | A1 | 11/1989 |
| WO | WO-9008260 | A1 | 7/1990 |
| WO | WO-9729282 | A1 | 8/1997 |
| WO | WO-9959652 | A1 | 11/1999 |
| WO | WO-0037126 | A1 | 6/2000 |
| WO | WO-0074747 | A1 | 12/2000 |
| WO | WO-2007053881 | A1 | 5/2007 |
| WO | WO-2009094188 | A2 | 7/2009 |
| WO | WO-2011056823 | A2 | 5/2011 |
| WO | WO-2016179262 | A1 | 11/2016 |
| WO | WO-2017087717 | A1 | 5/2017 |
| WO | WO-2017087785 | A1 | 5/2017 |
| WO | WO-2019019206 | A1 | 1/2019 |
| WO | WO-2019092175 | A1 | 5/2019 |
| WO | WO-2019154804 | A1 | 8/2019 |
| WO | WO-2020115607 | A2 | 6/2020 |
| WO | WO-2025215486 | A1 | 10/2025 |

OTHER PUBLICATIONS

U.S. Appl. No. 15/484,101 / U.S. Pat. No. 9,968,720, filed Apr. 10, 2017 / May 15, 2018.

U.S. Appl. No. 15/484,108 / U.S. Pat. No. 10,166,319, filed Apr. 10, 2017 / Jan. 1, 2019.

U.S. Appl. No. 15/940,856 / U.S. Pat. No. 10,933,181, filed Mar. 29, 2018 / Mar. 2, 2021.

U.S. Appl. No. 15/953,269 / U.S. Pat. No. 10,188,779, filed Apr. 13, 2018 / Jan. 29, 2019.

U.S. Appl. No. 15/976,831 / U.S. Pat. No. 10,398,821, filed May 10, 2018 / Sep. 3, 2019.

U.S. Appl. No. 16/234,519 / U.S. Pat. No. 11,097,091, filed Dec. 27, 2018 / Aug. 24, 2021.

U.S. Appl. No. 16/557,711 / U.S. Pat. No. 11,298,522, filed Aug. 30, 2019 / Aug. 30, 2019.

U.S. Appl. No. 16/762,909 / U.S. Pat. No. 11,512,689, filed May 8, 2019 / Nov. 29, 2022.

U.S. Appl. No. 16/766,267 / U.S. Pat. No. 11,446,480, filed May 21, 2020 / Sep. 20, 2022.

U.S. Appl. No. 16/819,021 / U.S. Pat. No. 10,799,625, filed Mar. 13, 2020 / Oct. 31, 2020.

U.S. Appl. No. 17/179,961 / U.S. Pat. No. 11,623,077, filed Feb. 19, 2021 / Apr. 11, 2023.

U.S. Appl. No. 17/193,867 / U.S. Pat. No. 11,191,946, filed Mar. 5, 2021 / Dec. 7, 2021.

U.S. Appl. No. 17/299,749, filed Jun. 3, 2021.

U.S. Appl. No. 17/409,100 / U.S. Pat. No. 11,712,554, filed Aug. 23, 2021 / Aug. 1, 2023.

U.S. Appl. No. 17/474,935, filed Sep. 14, 2021.

U.S. Appl. No. 17/658,074 / U.S. Pat. No. 12,005,245, filed Apr. 5, 2022 / Jun. 11, 2024.

U.S. Appl. No. 17/930,404 / U.S. Pat. No. 12,214,182, filed Sep. 7, 2022 / Feb. 4, 2025.

U.S. Appl. No. 18/131,853, filed Apr. 6, 2023.

U.S. Appl. No. 18/306,021 / U.S. Pat. No. 12,251,550, filed Apr. 24, 2023 / Mar. 18, 2025.

U.S. Appl. No. 18/509,187 / U.S. Pat. No. 12,017,059, filed Nov. 14, 2023 / Jun. 25, 2024.

U.S. Appl. No. 18/664,247 / U.S. Pat. No. 12,257,427, filed May 14, 2024 / Mar. 25, 2025.

U.S. Appl. No. 18/676,020, filed May 28, 2024.

U.S. Appl. No. 19/044,561, filed Feb. 3, 2025.

U.S. Appl. No. 19/076,730, filed Mar. 11, 2025.

U.S. Appl. No. 19/086,860, filed Mar. 21, 2025.

Ando, et al., Electrocardiogram-Synchronized Rotational Speed Change Mode in Rotary Pumps Could Improve Pulsatility, Artificial Organs, 35(10):941-947 (2011).

Ando, et al., Left ventricular decompression through a patent foramen ovale in a patient with hypertrophic cardiomyopathy: A case report, Cardiovascular Ultrasound, 2: 1-7 (2004).

Bozkurt, et al., Improving Arterial Pulsatility by Feedback Control of a Continuous Flow Left Ventricular Assist Device via in silico Modeling, International Journal of Artificial Organs, 37(10):773-785 (2014).

Castellanos, et al., Generations of Left Ventricular Assist Devices: The HeartMate Family, Dept. of Bioengineering. Florida Gulf Coast University, BME 3100C, pp. 1-6. (No date available).

Crow, et al., Gastrointestinal Bleeding Rates in Recipients of Nonpulsatile and Pulsatile Left Ventricular Assist Devices, The Journal of Thoracic and Cardiovascular Surgery, 137(1):208-215 (2009).

Extended European Search Report dated Aug. 25, 2021 in EP Patent Application Serial No. 21168340.4 (0231).

Fatullayev, et al., Continuous-Flow Left Ventricular Assist Device Thrombosis: A Danger Foreseen is a Danger Avoided, Medical Science Monitor Basic Research, 21:141-144 (2015).

Feier, et al., A Novel, Valveless Ventricular Assist Device: The Fish Tail Pump. First Experimental in Vivo Studies, Artificial Organs, (26)12:1026-1031 (2002).

Fliess, et al., Flatness and Defect of Nonlinear Systems: Introductory Theory and Examples, International Journal of Control, 61(6):1327-1361 (1995).

Fraser et al., A Quantitative Comparison of Mechanical Blood Damage Parameters in Rotary Ventricular Assist Devices: Shear Stress, Exposure Time and Hemolysis Index, Journal of Biomechanical Engineering, 134(8):018002-1 to 018002-11 (2012).

Harris, et al., Ventricular Assist Devices, Continuing Education in Anesthesia, Critical Care & Pain, 12(3):145-151 (2012).

International Search Report & Written Opinion dated Mar. 4, 2019 in Int'l PCT Patent Appl. No. PCT/IB2018/059199, 13 pages (0510).

International Search Report & Written Opinion dated Apr. 2, 2024 in Int'l PCT Patent Appl. Serial No. PCT/IB2023/061509 (1310).

International Search Report & Written Opinion dated May 14, 2021 in Int'l PCT Patent Appl. Serial No. PCT/IB2021/051879 (0910).

International Search Report & Written Opinion dated Jun. 28, 2017 in Int'l PCT Patent Application Serial No. PCT/IB2017/052068 (0210).

International Search Report & Written Opinion dated Jul. 15, 2020 in Int'l PCT Patent Appl. Serial No. PCT/IB2019/060144 (0610).

International Search Report & Written Opinion dated Aug. 22, 2017 in Int'l PCT Patent Application Serial No. PCT/IB2017/052069 (0310).

International Search Report & Written Opinion dated Oct. 9, 2023 in Int'l PCT Patent Appl. Serial No. PCT/IB2023/054203 (1110).

International Search Report and Written Opinion dated Apr. 16, 2019 in Int'l PCT Patent Appl. Serial No. PCT/EP2018/080749 (English Translation of ISR only) (0810).

International Search Report and Written Opinion dated Jun. 25, 2020 in International PCT Patent Application Serial No. PCT/ 1B2020/052337 (0710 PCT).

International Search Report and Written Opinion dated Aug. 3, 2018 in Int'l PCT Patent Appl. Serial No. PCT/IB2018/052215 (0410).

Ising, M., RPM and Flow Modulation for a Continuous Flow Left Ventricular Assist Device to Increase Vascular Pulsatility: A Computer Simulation, Mock Circulation, and In-Vivo Animal Study, University of Louisville, Think IR: The University of Louisville's Institutional Repository, Electronic Theses and Dissertations (Jul. 2011).

(56) References Cited

OTHER PUBLICATIONS

Islam et al., Left Ventricular Assist Devices and Gastrointestinal Bleeding: A Narrative Review of Case Reports and Case Series, Clinical Cardiology, 36(4):190-200 (2013).
Jorde, et al., Identification and Management of Pump Thrombus in the HeartWare Left Ventricular Assist Device System, JACC: Heart Failure, 3(11):849-856 (2015).
Latham, et al., Parameter Estimation and a Series of Nonlinear Observers for the System Dynamics of a Linear Vapor Compressor, IEEE Transactions on Industrial Electronics, 63(11):6736-6744 (2016).
Leverett, et al., Red Blood Cell Damage by Shear Stress, Biophysical Journal, 12(3):257-273 (1972).
Malehsa, et al., Acquired von Willebrand Syndrome After Exchange of the HeartMate XVE to the HeartMate II Ventricular Assist Device, European Journal of Cardio-Thoracic Surgery, 35(6):1091-1093 (2009).
Mancini, et al., Left Ventricular Assist Devices, A Rapidly Evolving Alternative to Transplant, Journal of the American College of Cardiology, 653:2542-2555 (2015).
Mboup, et al., Numerical Differentiation With Annihilators in Noisy Environment, Numerical Algorithms, 50(4):439-467 (2009).
Menhour, et al., An Efficient Model-Free Setting for Longitudinal and Lateral Vehicle Control: Validation Through the Interconnected Pro-SiVIC/RTMaps Prototyping Platform, IEEE Transactions on Intelligent Transportation Systems, 19(2):461-475 (2018).
Mercorelli, P., A Motion-Sensorless Control for Intake Valves in Combustion Engines, IEEE Transactions on Industrial Electronics, 64(4):3402-3412 (2017).
Mercorelli, P., An Adaptive and Optimized Switching Observer for Sensorless Control of an Electromagnetic Valve Actuator in Camless Internal Combustion Engines, Asian Journal of Control, 16(4):959-973 (2014).
Mohite, et al., Does CircuLite Synergy Assist Device as Partial Ventricular Support have a Place in Modern Management of Advanced Heart Failure?, Expert Rev. Med. Devices, published online Dec. 2, 2014 (pp. 1-12).
Najjar, et al., An Analysis of Pump Thrombus Events in Patients in HeartWare Advance Bridge to Transplant and Continued Access Protocol Trial, The Journal of Heart and Lung Transplantation, 33(1):23-34 (2014).
Pagani, Francis D., MD, PhD, Department of Cardiac Surgery, University of Michigan, "Technology 101: Review of Current Technologies, Types of Flow, Pump Parameters," American Association for Thoracic Surgery, Annual Meeting (2014), Cardiothoracic Transplant and Mechanical Circulatory Support of Heart and Lung Failure.
Perschall, et al., The Progressive Wave Pump: Numerical Multiphysics Investigation of a Novel Pump Concept With Potential to Ventricular Assist Device Application, Artificial Organs, 35(9):E179-E190 (2012).
Rahman, et al., Position Estimation in Solenoid Actuators, IEEE Transactions on Industry Applications, 32(3):552-559 (1996).
Rigatos, G., Differential Flatness Theory ad Flatness-Based Control, in Nonlinear Control and Filtering Using Differential Flatness Approaches, 25(2):47-101 (2015).
Wang, et al., Rotary Blood Pump Control Strategy for Preventing Left Ventricular Suction, ASAIO Journal, 61(1):21-30(2015).
Wang., Quadrotor Analysis and Model Free Control with Comparisons, Universite Paris Sud—Paris XI, (2013).
Weidemann, Daniel., Thesis entitled, Permanent Magnet Reluctance Actuators for Vibration Testing, Completed at the Institute of Applied Mechanics, Technische Universitat Munchen, Apr. 2013.
Yuan, et al., The Spectrum of Complications Following Left Ventricular Assist Device Placement, Journal of Cardiac Surgery, 27:630-638 (2012).
Zhang, et al., Study on Self-Sensor of Linear Moving Magnet Compressor's Piston Stroke, IEEE Sensors Journal, 9(2):154-158 (2009).
Widhalm, et al., Enhancing Left Ventricular Assist Device Usability: A Comparative Simulation Study of CorWave and HeartMate 3 Peripherals, ASAIO Journal 2025, Adult Circulatory Support, pp. 2-11 (2025).
HeartMate II LVAS, Left Ventricular Assist System, Instructions for Use, Sep. 25, 2009.
Yuhki, et al., Detection of Suction and Regurgitation of the Implantable Centrifugal Pump Based on the Motor Current Waveform Analysis and Its Application to Optimization of Pump Flow, Artificial Organs, 23(6):532-537 (Jun. 1999).

* cited by examiner 708
700
706
702
704

708
700
706
702
704
712
710

700
702
704
706
712
710
716
708
720
718
714

700
702
704
706
712
710
716
708
720
724
722
718
714

SYSTEMS AND METHODS FOR POWERING AND CONTROLLING AN IMPLANTABLE HEART PUMP

CROSS-REFERENCE TO RELATED APPLICATIONS

This application claims priority to U.S. Provisional Patent App. No. 63/631,334, filed Apr. 8, 2024, and European Patent App. No. 24315131.3, filed Apr. 8, 2024, the entire contents of each of which are incorporated herein by reference.

TECHNICAL FIELD

This technology relates, in general, to heart pumps, and, more particularly, to systems and methods for powering and controlling implantable heart pumps.

BACKGROUND

The human heart is comprised of four major chambers with two ventricles and two atria. Generally, the right-side heart receives oxygen-poor blood from the body into the right atrium and pumps the oxygen-poor blood via the right ventricle to the lungs. The left-side heart receives oxygen-rich blood from the lungs into the left atrium and pumps the oxygen-rich blood via the left ventricle to the aorta for distribution throughout the body. Due to any of a number of illnesses, including coronary artery disease, high blood pressure (hypertension), valvular regurgitation and calcification, damage to the heart muscle as a result of infarction or ischemia, myocarditis, congenital heart defects, abnormal heart rhythms, or various infectious diseases, the left ventricle may be rendered less effective and thus unable to pump oxygenated blood throughout the body.

The Centers for Disease Control and Prevention (CDC) estimate that about 5.1 million people in the United States suffer from some form of heart failure. Heart failure is generally categorized into four different stages with the most severe being end-stage heart failure. End-stage heart failure may be diagnosed where a patient has heart failure symptoms at rest in spite of medical treatment. Patients at this stage may have systolic heart failure, characterized by decreasing ejection fraction. In patients with systolic heart failure, the walls of the ventricle, which are typically thick in a healthy patient, become thin and weak. Consequently, during systole, a reduced volume of oxygenated blood is ejected into circulation, a situation that continues in a downward spiral until death. A patient diagnosed with end-stage heart failure has a one-year mortality rate of approximately fifty percent (50%).

For patients who have reached end-stage heart failure, treatment options are limited. In addition to continued use of drug therapy commonly prescribed during earlier stages of heart failure, the typical recommendation is cardiac transplantation and implantation of a mechanical assist device. While a cardiac transplant may significantly prolong the patient's life beyond the one-year mortality rate, patients frequently expire while on a waitlist for months, sometimes years, awaiting a suitable donor heart. Presently, the only alternative to a cardiac transplant is a mechanical implant. While in recent years mechanical implants have improved in design, typically, such implants will prolong a patient's life by a few years, at most, and include a number of co-morbiditics.

One type of mechanical implant often used for patients with end-stage heart failure is a left ventricular assist device (LVAD). An LVAD is a surgically-implanted pump that draws oxygenated blood from the left ventricle and pumps the oxygenated blood directly to the aorta, thereby off-loading (reducing) the pumping work of the left ventricle. LVADs are typically used as either "bridge-to-transplant therapy" or "destination therapy." When used for bridge-to-transplant therapy, the LVAD is used to prolong the life of a patient who is waiting for a heart transplant. When a patient is not suitable for a heart transplant, the LVAD may be used as a destination therapy to prolong the life, or improve the quality of life, of the patient, but generally such prolongation is for only a couple years.

Existing systems and methods for powering and controlling implantable heart pumps such as LVADs suffer from a number of shortcomings that often prove detrimental (and may, in some instances, even be life-threatening) to users of such implantable heart pumps. For example, existing controllers used to control and/or direct power to implantable heart pumps often inadequately consider the potentially diminished physical capabilities of their users. When a battery installed in a controller and used to power the controller and/or an implantable heart pump becomes depleted, for instance, a user may experience difficulty in removing the battery from the controller in order to install a replacement battery. A mechanism used to unlock the battery from the controller may be overly stiff or rigid, which may require the user to apply a depressive force exceeding his or her grip strength simply to detach the battery from the controller. The controller may even require that the user simultaneously depress multiple buttons or other mechanisms in a particular manner to unlock the battery (e.g., by holding the controller in a specific orientation), which may prove challenging or even impossible for a user with limited dexterity or hand function. Further still, the mechanism used to unlock the battery from the controller may not provide adequate tactile feedback to the user, which may prevent the user from recognizing when the mechanism has actually unlocked the battery from the controller.

In the event that the user is able to unlock the battery from the controller, a number of drop hazards may arise. For one, the controller and/or battery may have smooth or slippery surfaces, which may present a risk that the user will unintentionally drop the controller and/or battery during handling. Moreover, once unlocked, the battery and controller may lack any mechanism for keeping the battery from falling out of the controller under its own weight before the user is able to manually and intentionally remove the battery from the controller. As will be understood, such hazards are likely to be exacerbated for users whose response times are delayed by any number of physical limitations.

Further still, existing systems for powering implantable heart pumps lack robust and interchangeable power-supply options, which may increase costs and decrease reliable access to power for these life-saving devices. For example, with respect to portable power supplies, typical systems do not include both a high-capacity battery connected integrally to a controller and an optional separate, or tethered, battery, which only limits "excursion" time for the user to that provided on a single battery charge. In the event that the controller used with the implantable heart pump may receive power from both an integrally-connected battery and a tethered battery, the integrally-connected battery is likely to have an entirely different interface from the tethered battery, thus preventing interchangeability of the two batteries (e.g., in case of a faulty connection to one battery receptor or as a general matter) and requiring the user to maintain costly supplies of two separate types of batteries and associated components (e.g., battery chargers). Moreover, in the event that the controller can receive power from a tethered battery, the connection to the tethered battery is likely to differ from a separate connection available for receiving power from a grid-based power supply (e.g., via AC wall outlet and AC/DC power adapter). As such, the controller must include two separate power ports, one for tethered battery power and the other for plug-in/grid power, which will increase the necessary size of the controller and add additional components subject to failure. As yet another limitation of existing systems, any mechanism used to lock a battery to the controller is typically integral to the controller (rather than the battery). Because any such mechanism is likely subject to a significant degree of wear and eventual failure, there is a high likelihood that the controller will need to be taken out of service to replace failed parts, in which case a backup controller may not be readily available.

Thus, improved systems and methods for powering and controlling implantable heart pumps that offer better ergonomics and more robust power-supply options are needed.

SUMMARY

The technology described herein overcomes the drawbacks of previously-known systems and methods for powering and controlling implantable heart pumps by providing improved systems and methods that are more conducive to use by typical users of implantable heart pumps, many of whom may be limited by compromised physical abilities, mobility issues, and other restraints. For example, the systems and methods for powering and controlling implantable heart pumps described herein may offer improved operational flexibility, ergonomics, and failsafe mechanisms corresponding to expected (e.g., diminished or compromised) physical capabilities of users, more robust and interchangeable power-sourcing between battery and main power supplies to increase "excursion" time and/or to offer reliable backup power under various conditions, and numerous other benefits that will become apparent throughout this disclosure.

In accordance with one aspect, a system for powering and controlling an implantable heart pump may include an external controller housing designed to house a processor that may be programmed to control the implantable heart pump, a battery housing designed to be removably attached to the external controller housing and to house battery cells to supply power to the implantable heart pump, a button connected to the battery housing, and a latch extending from the button to a latch protrusion. The external controller housing may include a latch receiver. The button may be designed to be biased away from the battery housing in a locked position. In the locked position, the latch protrusion may engage with the latch receiver to lock the external controller housing to the battery housing. The button may further be designed to be depressed toward the battery housing to cause the latch protrusion to disengage from the latch receiver to permit the battery housing to be detached and removed from the external controller housing.

The system may further include a spring positioned between the button and the battery housing. The spring may be designed to bias the button away from the battery housing by a distance determined to provide a tactile feedback to a user of the implantable heart pump when the button is sufficiently depressed to cause the latch protrusion to disengage from the latch receiver. The button may be further designed to be depressed toward the battery housing to cause the latch protrusion to disengage from the latch receiver by applying a depressive force corresponding to an expected grip strength of the user of the implantable heart pump. The button may be a single button designed to permit the battery housing to be detached and removed from the external controller housing when the single button is depressed toward the battery housing. The button may further be designed to be depressed single-handedly by either a thumb or one or more fingers of the user.

At least one of the external controller housing or the battery housing may include a retainer. The retainer may be designed to retain the battery housing to the external controller housing in an unlocked position, by applying a retentive force, to prevent unintended detachment of the battery housing from the external controller housing. The retainer may further be designed to permit the user to detach and remove the battery housing from the external controller housing in the unlocked position. The retainer may include, for example, one or more retention springs, one or more friction surfaces, or one or more sets of magnets. At least one of the external controller housing or the battery housing may include one or more guides to direct the battery housing to engage with the external controller housing such that corresponding electrical contacts of the battery cells housed in the battery housing and of the external controller housing may engage with one another when the battery housing is attached to the external controller housing.

The external controller housing may further be designed to house a reserve battery designed to supply power to the implantable heart pump when the battery cells in the battery housing are not supplying power to the implantable heart pump (e.g., when the battery cells are being replaced or the battery housing is being exchanged). The system may further include a tethered housing designed to receive a supplemental battery housing and to be removably attached to the external controller housing via a tethering cable. The supplemental battery housing may be designed to house supplemental battery cells to supply power to the implantable heart pump via the tethering cable. The tethering cable may be connected to the tethered housing at one end and may include a connector designed to be removably connected to a power port of the external controller housing at another end. The power port may be designed to interchangeably receive power from the supplemental battery cells via the tethering cable or from an external power supply such that the implantable heart pump may thereby receive power from the supplemental battery cells or the external power supply, either alone or in combination with the battery cells in the battery housing (although it will further be understood that, in some arrangements, operation of the system may nonetheless require that the battery housing and/or associated battery cells remain attached or connected to the external controller housing, for instance, to prevent undesired exposure of internal electrical connections). The battery housing may further be designed to be removably attached to the tethered housing. The supplemental battery housing may further be designed to be removably attached to the external controller housing.

The external controller housing may include a user interface designed to provide information on the implantable heart pump to the user. The system may include the implantable heart pump. The system may further include a percutaneous cable designed to be connected to the external controller housing, to extend through skin of the user, and to be connected to the implantable heart pump.

In accordance with another aspect, an implantable heart pump may be powered and controlled. For example, a battery housing designed to house battery cells to supply power to the implantable heart pump may be selected. A button may be connected to the battery housing. A latch may extend from the button to a latch protrusion. The battery housing may be attached to an external controller housing such that the latch protrusion engages a latch receiver of the external controller housing to thereby lock the battery housing to the external controller housing. The external controller housing may be designed to house a processor that may be programmed to control the implantable heart pump. The battery cells may be permitted to supply power to the implantable heart pump until a time to replace the battery cells. The button may be depressed toward the battery housing to cause the latch protrusion to disengage from the latch receiver. While the button is depressed, the battery housing may be removed from the external controller housing. The battery cells may be replaced with a new set of battery cells for connecting to the external controller housing in order to supply power to the implantable heart pump.

DETAILED DESCRIPTION

Systems and methods for powering and controlling implantable heart pumps are provided. A system for powering and controlling an implantable heart pump may include an external controller housing designed to house a processor that may be programmed to control the implantable heart pump, a battery housing designed to be removably attached to the external controller housing and to house battery cells to supply power to the implantable heart pump, a button connected to the battery housing, and a latch extending from the button to a latch protrusion. The external controller housing may include a latch receiver. The button may be designed to be biased away from the battery housing in a locked position. In the locked position, the latch protrusion may engage with the latch receiver to lock the external controller housing to the battery housing. The button may further be designed to be depressed toward the battery housing to cause the latch protrusion to disengage from the latch receiver to permit the battery housing to be detached and removed from the external controller housing.

The system may have various features included to offer improved usability for an expected user of the implantable heart pump (e.g., a typical LVAD patient). For example, the system may include various features designed to provide tactile feedback or comfortable ergonomics to a user during operation of the system. Forces necessary to perform certain tasks associated with the system (e.g., depressing the button or removing the battery housing from the external controller housing) may be determined based on expected strength of the user in view of likely physical limitations. A retainer may be provided to prevent unintended detachment of the battery housing from the external controller housing. The system may provide interchangeable and customizable options for supplying power to the implantable heart pump and/or a corresponding controller in a range of circumstances, for example, via integral, locally-connected, tethered, and/or grid-sourced power. These and other improvements over existing systems and methods will become apparent in view of the following disclosure.

Figure 1A:
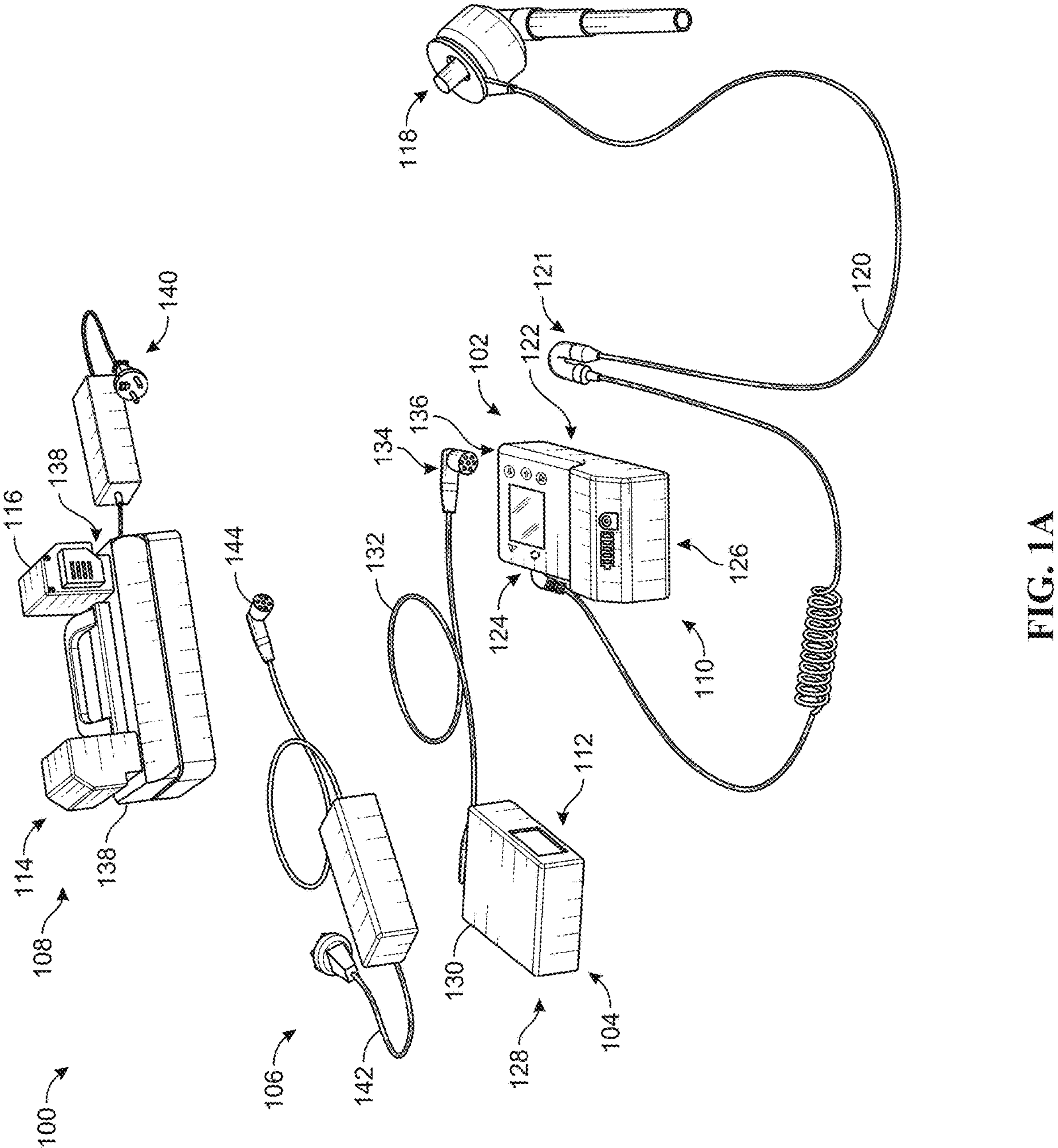
FIGS. 1A-1B are perspective views of an exemplary system for powering and controlling an implantable heart pump.
Figure 1B:
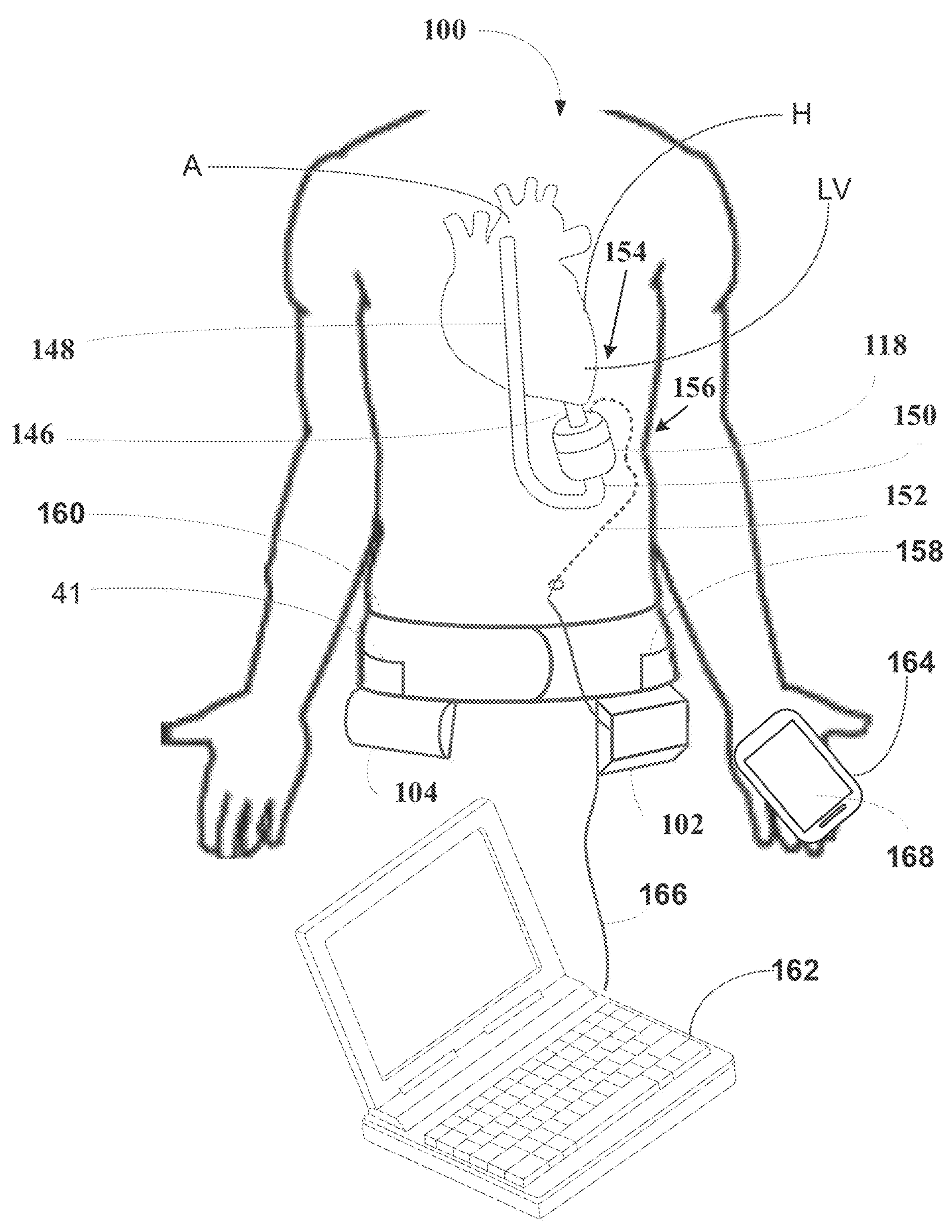

Referring now to FIGS. 1A-1B, and in brief overview, a system for powering and controlling an implantable heart pump is illustrated. As shown in FIG. 1A, system 100 may include controller 102, tethered power adapter 104, external power adapter 106, battery charger 108, and/or one or more batteries 110, 112, 114, 116. Controller 102 may be connected to and/or control implantable pump 118 via cabling 120. Implantable pump 118 may or may not be a component of system 100.

Controller 102 may include external controller housing 122 for housing a processor (not shown). The processor may be programmable to control implantable pump 118. External controller housing 122 may include user interface 124 for providing information on implantable pump 118 to a user. Cabling 120 may include a percutaneous cable designed to be connected to external controller housing 122 at one end, to extend through skin of a user, and to be connected to implantable pump 118 at another end. Implantable pump 118 may receive control signals from controller 102 via cabling 120, which may include connector 121 to facilitate communication between the portions of cabling 120 connected, respectively, to external controller housing 122 and implantable pump 118.

Any combination of batteries 110, 112, 114, and/or 116 may be used to supply power to implantable pump 118 via controller 102, either alone or in combination with an external power supply, which may serve to extend a potential "excursion" time for a user of implantable pump 118 relying on battery power and/or to provide for a range of options for sourcing power to implantable pump 118 in various situations (e.g., in case of an emergency requiring transportation of the user to a hospital and thus requiring disconnection from any main or hardwired power supply).

For example, battery 110 may include battery housing 126 designed to house one or more battery cells (not shown). Battery housing 126 may be removably attachable to external controller housing 122. As such, the battery cell(s) housed in battery housing 126 may supply power to implantable pump 118 via one or more electrical connections between battery 110, controller 102, and implantable pump 118. Alternatively, or in addition, battery 112 may be a supplemental battery and may include battery housing 128 designed to house one or more supplemental battery cells (not shown). Battery housing 128 may be removably attachable to tethered housing 130 of tethered power adapter 104. Tethered power adapter 104 may be connected to controller 102 via tethering cable 132. For example, tethering cable 132 may be connected to tethered housing 130 at one end and include connector 134 at another end. Connector 134 may be removably connectable to power port 136 of external controller housing 122. Power port 136 may be designed to interchangeably receive power from one or more sources of battery or main power (e.g., battery power or an external power supply). As such, the battery cell(s) housed in battery housing 128 may supply power to implantable pump 118 (either as a primary, supplemental, or backup source of power) via one or more electrical connections between battery 112, tethered power adapter 104, controller 102, and implantable pump 118.

The respective battery housings of batteries 110, 112, 114, and/or 116 may be interchangeably attachable to external controller housing 122 of controller 102 and/or tethered housing 130 of tethered power adapter 104 for supplying power to implantable pump 118 in a flexible and adaptable manner. For example, battery 110 may be removably attachable to (and used to supply power to implantable pump 118 via) tethered power adapter 104, while battery 112 may be removably attachable to (and used to supply power to implantable pump 118 via) controller 102. Batteries 114 and/or 116 may be spare batteries to be used interchangeably with battery 110 and/or 112. Battery charger 108 may include one or more charging ports 138 to receive and recharge any of batteries 110, 112, 114, and/or 116, when depleted and not in use, using power supplied from an external power supply via battery charger power supply cable 140. Controller 102 may further house a reserve battery (not shown) within external controller housing 122 to supply power to implantable pump 118 when none of batteries 110, 112, 114, or 116 are supplying power to implantable heart pump, for instance, due to charge depletion of their respective battery cells, poor electrical connection, or any other powering issue. Accordingly, a user of system 100 may enjoy a range of options for portably powering implantable pump 118 via battery power.

External power adapter 106 may be provided to supply power to implantable pump 118, either alone or in combination with any of batteries 110, 112, 114, and/or 116. For example, external power adapter 106 may be connected to an external power supply (e.g., main, hardwired, or AC power; not shown) at one end via external power supply cable 142. At another end, external power adapter 106 may be removably connected to power port 136 of external controller housing 122 via connector 144. As such, the external power supply may supply power to implantable pump 118 via one or more electrical connections between external power adapter 106, controller 102, and implantable pump 118.

It will be understood that any of the power supplies described herein (e.g., battery or external power supply) may be used in any number of combinations to supply power to implantable pump 118. For example, battery 110 may be attached to controller 102 and thereby serve as a "primary" source of battery power for implantable pump 118 without controller 102 being connected to any external or supplemental power supply. Alternatively, a different hardwired or portable power supply may be connected to power port 136 of external controller housing 122 to thereby supply power to implantable pump 118 in conjunction with (or instead of) battery 110. As one example, an external (e.g., hardwired or AC) power supply may supply "primary" power to implantable pump 118 via external power adapter 106 connected to power port 136, while battery 110 may serve as a "backup" source of power (or may not be used or included at all). This may be preferable, for instance, where a user of implantable pump 118 is confined to a hospital bed or localized homecare with a reliable source of AC power via a wall plug. As another example, battery 112 may supply "supplemental" power to implantable pump 118 via tethered power adapter 104 connected to power port 136, while battery 110 may serve as a "primary" source of power (or vice versa). As still another variation on the preceding example, batteries 110 and 112 may supply "tethered" power to implantable pump 118 such that batteries 110 and 112 alternate in supplying power to implantable pump 118 so as to deplete the two batteries according to a preferred depletion order or schedule (e.g., battery 112 before battery 110, or vice versa) or to deplete both batteries at a reasonably uniform rate. Either of the latter two setups may be preferable, for instance, where the user is more mobile, whether owing to general health or capability or as required due to extenuating circumstances (e.g., a healthcare-related emergency requiring travel to a hospital). It will further be understood that connector 144 of external power adapter 106 may be similar or identical in design to connector 134 of tethered power adapter 104, which may provide for the interchangeable availability of an external power supply (e.g., hardwired or AC power) or tethered battery power as needed or otherwise preferred. In these and other possible configurations, the reserve battery housed in external controller housing 122 may serve as an emergency power supply to implantable pump 118 in the event that power is unavailable from any other power source.

As shown in FIG. 1B, implantable pump 118 may be designed to be implanted within a patient's chest such that inlet cannula 146 may be connected to left ventricle LV of heart H. Outlet cannula 148 of implantable pump 118 may be connected to aorta A. Inlet cannula 146 may be connected to an apex of left ventricle LV, while outlet cannula 148 may be connected to aorta A in a vicinity of the ascending aorta, above a level of cardiac arteries. Implantable pump 118 may be affixed within the patient's chest using a ring suture or another conventional technique. Outlet cannula 148, which may include a Dacron graft or another synthetic material, may be connected to outlet 150 of implantable pump 118.

Controller 102 and/or tethered power adapter 104 may be extracorporeal and may be sized so as to be placed on a belt or garment worn by the patient. Controller 102 and/or tethered power adapter 104 may be electrically connected to implantable pump 118, for example, via cable 152 that may extend through a percutaneous opening in the patient's skin and into electrical conduit 154 of pump housing 156 of implantable pump 118. Illustratively, tethered power adapter 104 may be electrically connected to controller 102 via cable 158 that may be integrated into belt 160. Alternatively, controller 102 may be enclosed within a biocompatible housing and sized to be implanted subcutaneously in the patient's abdomen. In this alternative embodiment, controller 102 may include a wireless transceiver for bi-directional communications with an extracorporeal programming device and may also include a battery that is continuously and inductively charged via tethered power adapter 104 and an extracorporeal charging circuit. As will be understood, the foregoing alternative may avoid the use of percutaneous cable 152 and thereby eliminate a frequent source of infection with conventional LVADs.

Controller 102 and/or tethered power adapter 104 may each be designed to receive a rechargeable battery (e.g., battery 110 or 112) capable of powering implantable pump 118 and controller 102, either individually or in combination, for a period of several days (e.g., three to five days) before needing to be recharged. A separate charging circuit (e.g., battery charger 108) may be provided for recharging the one or more rechargeable batteries. Controller 102 and/or tethered power adapter 104 may each be contained in a housing (e.g., external controller housing 122 or tethered housing 130) suitable for carrying on a belt or holster so as not to interfere with the patient's daily activities.

System 100 may further include programmer 162 and/or a software module programmed to run on mobile device 164. Programmer 162 may be connected to controller 102 via cable 164. Programmer 162 may be, for example, a conventional laptop computer that is programmed to execute programmed software routines, for use by a clinician or medical professional, for configuring and providing operational parameters to controller 102. The configuration and operational parameter data may be stored in a memory associated with controller 102 and may be used by controller 102 to control operation of implantable pump 118. Controller 102 may direct implantable pump 118 to operate at specific parameters determined by programmer 162. Programmer 162 may only occasionally be connected to controller 102 via cable 166, for instance, when the operational parameters of implantable pump 118 are initially set or periodically adjusted (e.g., when the patient visits the clinician).

Mobile device 164, which may be a conventional smartphone, may include an application program for bi-directionally and wirelessly communicating with controller 102 (e.g., via Wi-Fi or Bluetooth communication). The application program on mobile device 164 may be programmed to permit the patient to send instructions to controller 102 to modify or adjust a limited number of operational parameters of implantable pump 118 stored in controller 102. Alternatively, or in addition, mobile device 164 may be programmed to receive from controller 102, and to display on screen 168 of mobile device 164, data relating to operation of implantable pump 118 and/or alert or status messages generated by controller 102.

Further details relating to example implantable heart pumps and corresponding systems, devices, and/or components that may be compatible with or otherwise provide further context in relation to the present technology are described throughout U.S. Pat. No. 9,968,720 to Botterbusch et al., U.S. Pat. No. 10,188,779 to Polverelli et al., U.S. Pat. No. 10,799,625 to Scheffler et al., U.S. Pat. No. 12,251,550 to Quelenn et al., U.S. Pat. No. 12,257,427 to Snyder et al., the entire contents of each of which are incorporated herein by reference.

Figure 2A:
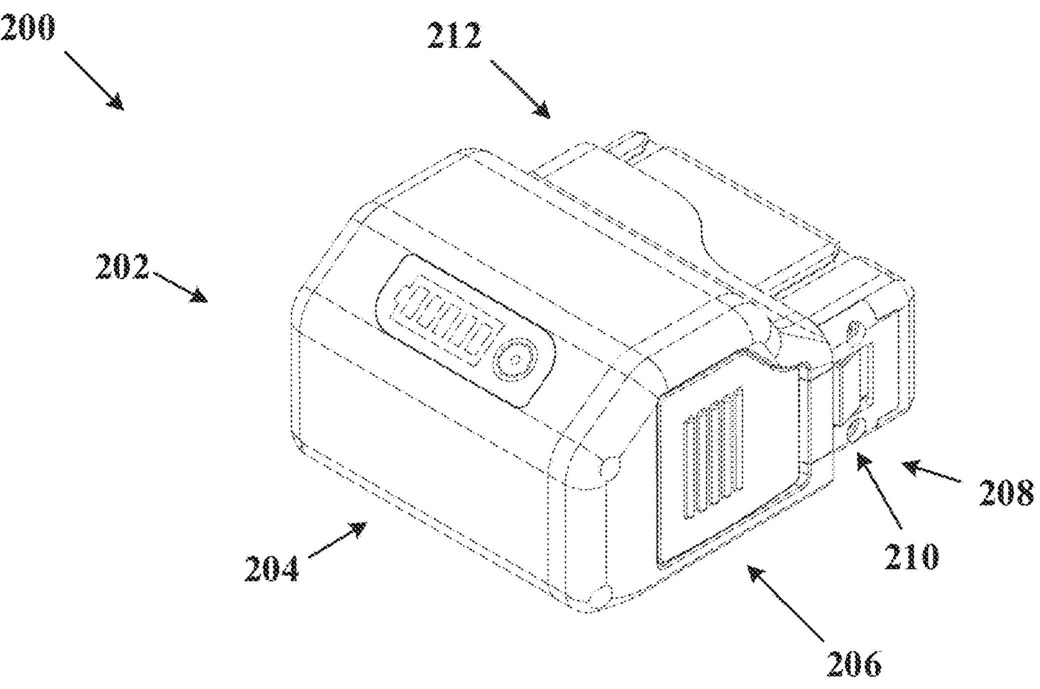
FIGS. 2A-2B are perspective views of an exemplary battery housing and an exemplary external controller housing that may be used in an implantable heart pump system.
Figure 2B:
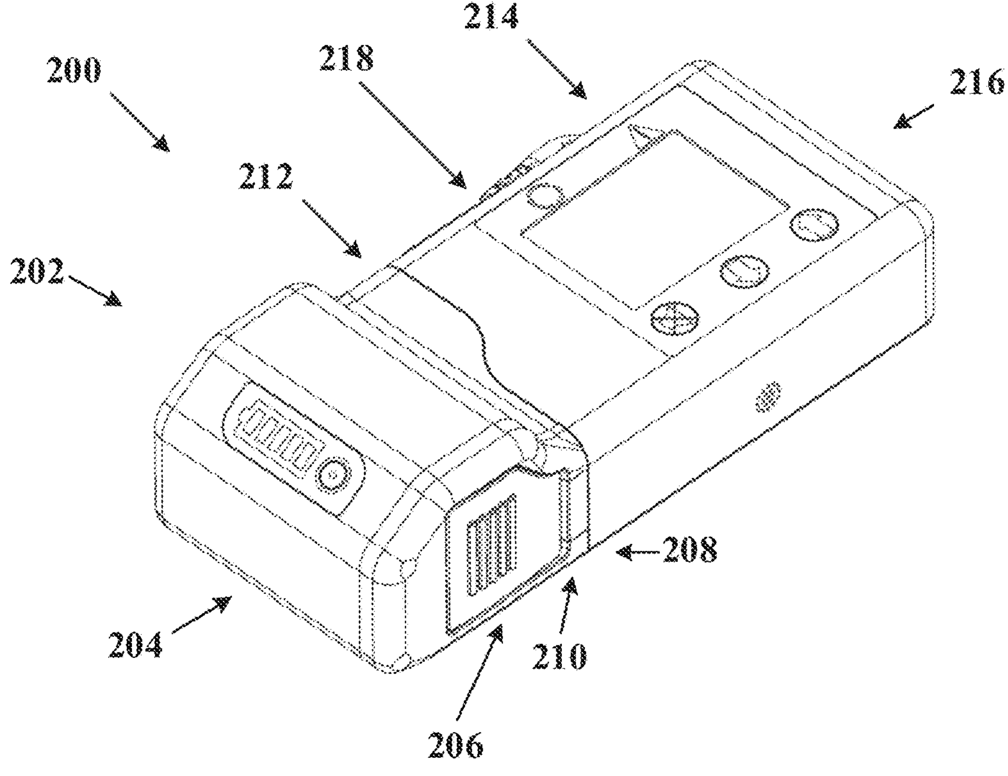

Referring now to FIGS. 2A-2B, and in brief overview, a battery and a controller compatible with a system for powering and controlling an implantable heart pump are illustrated. As shown in FIG. 2A, system 200 may include battery 202. Battery 202 may include battery housing 204, which may be designed to house one or more battery cells (not shown) to supply power to an implantable heart pump (not shown). Battery housing 204 may be connected to button 206. Latch 208 may extend from button 206 to latch protrusion 210 along extruded portion 212 of battery 202.

As shown in FIG. 2B, system 200 may further include controller 214. Controller 214 may include external controller housing 216. External controller housing 216 may be connected to cabling 218 and may be designed to house a processor that is programmable to control the implantable heart pump via cabling 218. The implantable heart pump may further receive power from one or more sources (e.g., battery 202) via cabling 218.

Controller 214 may be designed to receive battery 202. For example, external controller housing 216 of controller 214 may define a hollow internal cavity (not shown) around which extruded portion 212 of battery housing 204 of battery 202 may tightly interface. External controller housing 214 may include a latch receiver (not shown) corresponding to latch protrusion 210. Battery housing 204 may have "locked" and "unlocked" positions corresponding to relative positions of button 206. For example, button 206 may be designed to be biased away from battery housing 204 in the locked position. In the locked position, latch protrusion 210 may engage with the latch receiver such that battery housing 204 may be locked in place with respect to external controller housing 216. Button 206 may further be designed to be depressed toward battery housing 204 by a user to cause latch protrusion 210 to disengage from the latch receiver. In this manner, battery housing 204 may be transitioned to the unlocked position. In the unlocked position, the user may be permitted to detach and remove battery housing 204 from external controller housing 216 by manually applying force. Accordingly, battery 202 may be removed from controller 214 for purposes of recharging and/or replacement.

As further detailed below, button 206 and corresponding functionalities for locking or unlocking battery housing 204 relative to external controller housing 216 may be optimized for use by typical LVAD patients, many of whom may possess diminished physical capabilities (e.g., tactile sensitivity, grip strength, or dexterity). For example, button 206 may be designed to be biased away from battery housing 204 by a distance determined to provide a recognizable tactile feedback to a typical user of the implantable heart pump (e.g., a typical LVAD patient) when button 206 is sufficiently depressed to cause latch protrusion 210 to disengage from the latch receiver (i.e., when battery housing 204 is in the unlocked position) without unduly oversizing button 206, battery housing 204, and/or associated components or mechanisms. Alternatively, or in addition, button 206 may be designed to be depressed toward battery housing 204 to cause latch protrusion 210 to disengage from the latch receiver (i.e., to cause battery housing 204 to transition to the unlocked position) by applying a depressive force that corresponds to an expected grip strength of a typical user of the implantable heart pump. As still another example, button 206 may be designed to be depressed by users exhibiting limited dexterity. For instance, button 206 may be a single button needed to transition battery housing 204 to the unlocked position (as opposed to battery housings used with existing controllers, which typically require depression of multiple buttons to separate battery housing from controller). In other words, only a single button may need to be depressed to permit detachment and removal of battery housing 204 from external controller housing 216 when that single button is depressed toward battery housing 204. Further, unlike existing designs requiring the use of multiple hands to unlock a battery housing from a controller, button 206 may be designed such that a user may depress button 206 single-handedly (e.g., using either a thumb or one or more fingers) while safely maintaining a grip on battery 202 and/or controller 214.

Figure 3A:
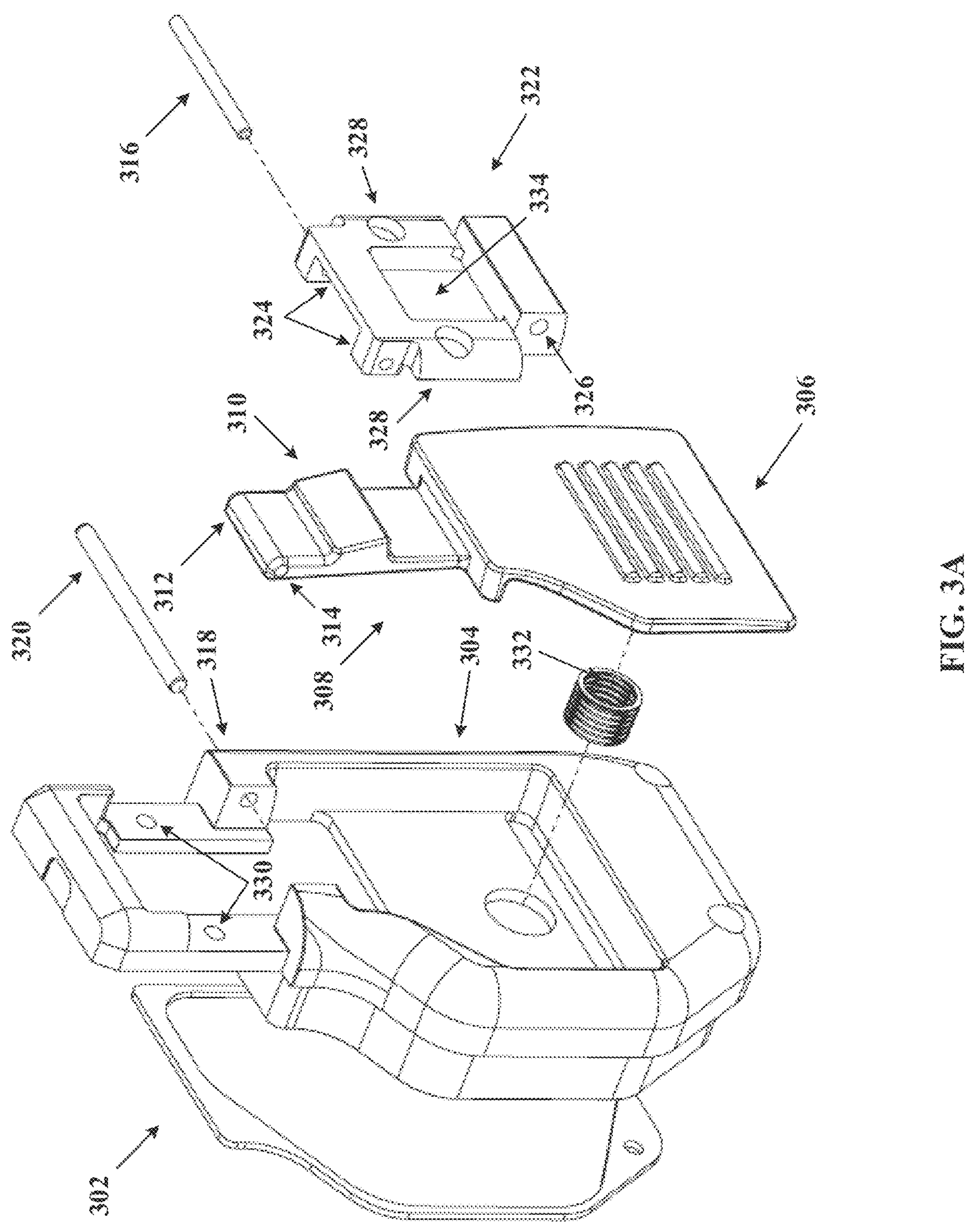
FIGS. 3A-3L are perspective and other views of the exemplary battery housing and external controller housing.
Figure 3C:
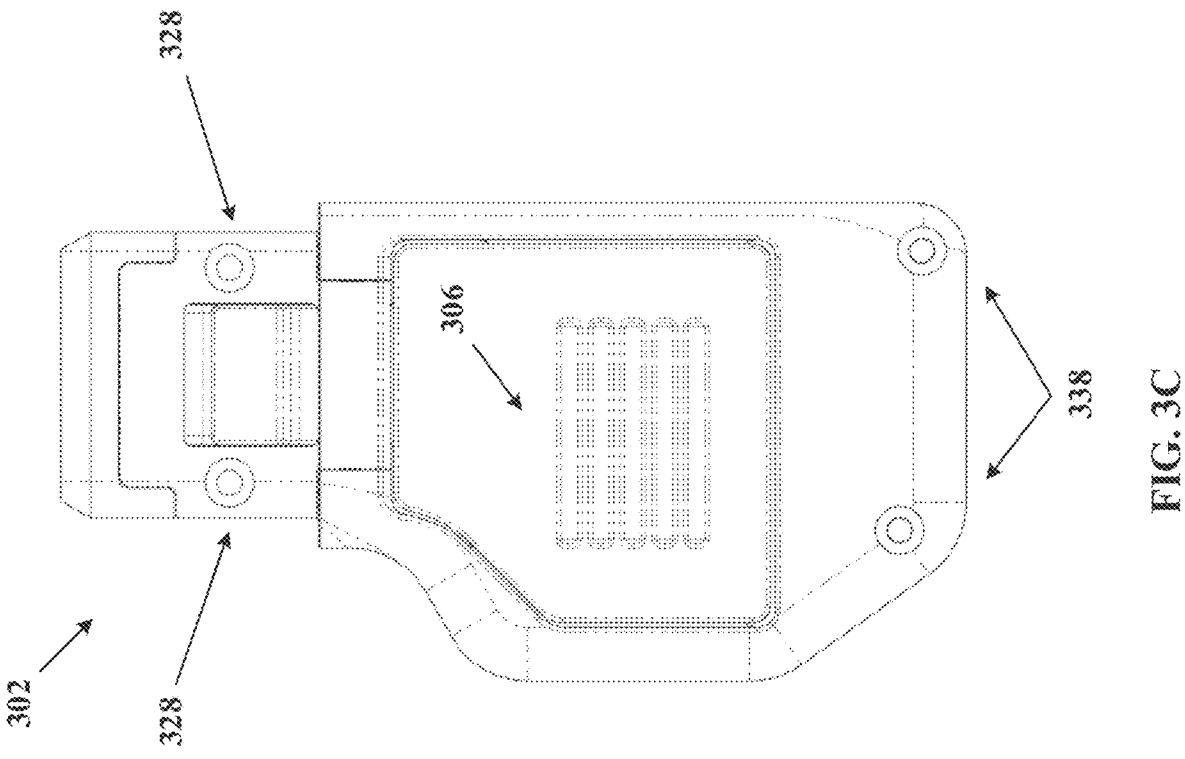
Figure 3B:
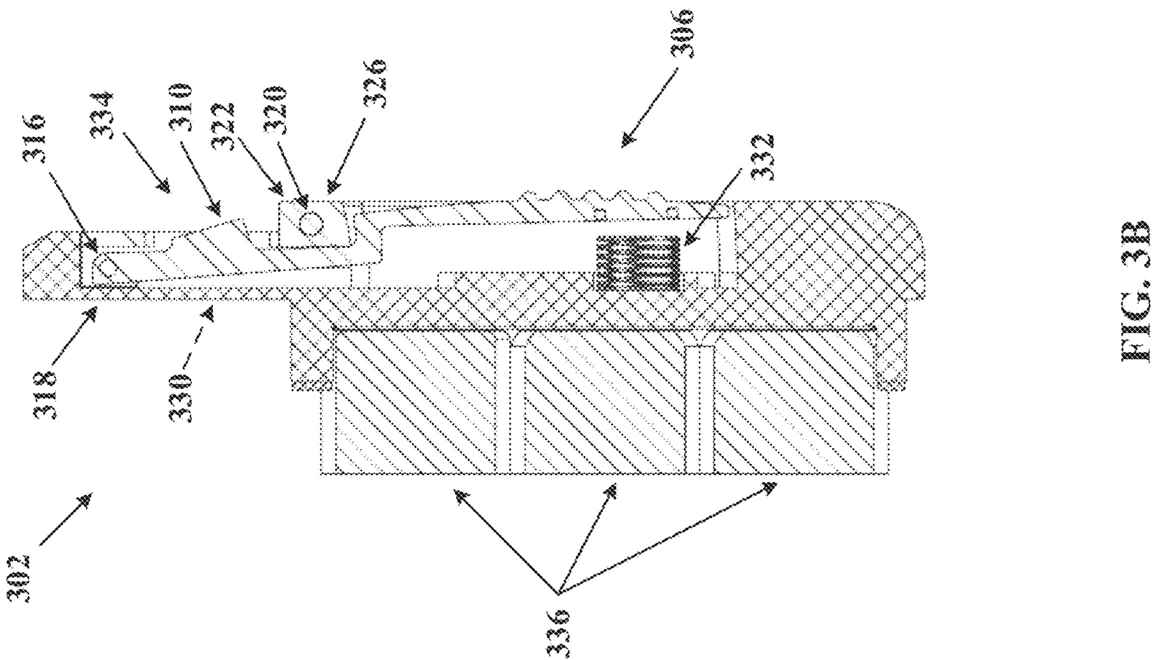

Referring now to FIGS. 3A-3L, and in brief overview, a battery and a controller compatible with a system for powering and controlling an implantable heart pump are illustrated. As shown in FIGS. 3A-3C, a battery housing of a battery designed to supply power to an implantable heart may include end cap 302 defining recessed portion 304. Recessed portion 304 may be designed to receive button 306. Latch 308 may extend from button 306 to latch protrusion 310, which may further extend to hinge 312. Hinge 312 may define channel 314 designed to receive pivot rod 316. End cap 302 may define channel 318 designed to receive limiting rod 320. Fixture piece 322 may be designed to movably secure button 306 and connected components to end cap 302. For example, fixture piece 322 may define holes 324 designed to be concentrically positioned with respect to channel 314 and to receive pivot rod 316 along with channel 314, thereby securing button 306 to fixture piece 322 while maintaining a degree of rotational freedom for button 306 and latch 308. Recessed portion 304 of end cap 302 may further be designed to receive fixture piece 322. Fixture piece 322 may further define channel 326 designed to be concentrically positioned with respect to channel 318 and to receive limiting rod 320 along with channel 318, thereby securing fixture piece 322 to end cap 302 and limiting the degree of rotational freedom for button 306 and latch 308 relative to a point of contact with fixture piece 322.

Fixture piece 322 may define one or more fastener holes 328 corresponding to one or more fastener holes 330 of end cap 302. Each pair of fastener holes 328 and 330 may be designed to be concentrically positioned to simultaneously receive a fastener (e.g., a screw or bolt; not shown) to thereby fasten fixture piece 322 to end cap 302. Each fastener may further extend and be fastened to a battery housing corresponding to end cap 302. Spring 332 may be positioned between button 306 and end cap 302 and may be designed to bias button 306 away from end cap 302. Latch protrusion 310 may extend through opening 334 defined by fixture piece 322 such that latch protrusion 310 may engage with latch receivers of various components (e.g., housings). End cap 302 may be further designed to secure one or more battery cells 336 within a battery housing. For example, end cap 302 may have one or more fastener holes 338 each designed to receive a fastener to secure end cap 302 to the battery housing.

Because various high-use components (e.g., button 306, spring 332, and/or latch 308) may be connected to an easily removable and replaceable component such as end cap 302 (as opposed to a more costly and integral component such as a controller of an implantable heart pump), maintenance related to operation of the implantable heart pump and the associated controller may be less burdensome. For example, should button 306, spring 332, and/or latch 308 wear out or fail due to ongoing use, a user need not take the entire controller out of service but may instead repair a few separable components of a battery for which a spare is likely available.

Figures 3D, 3E:
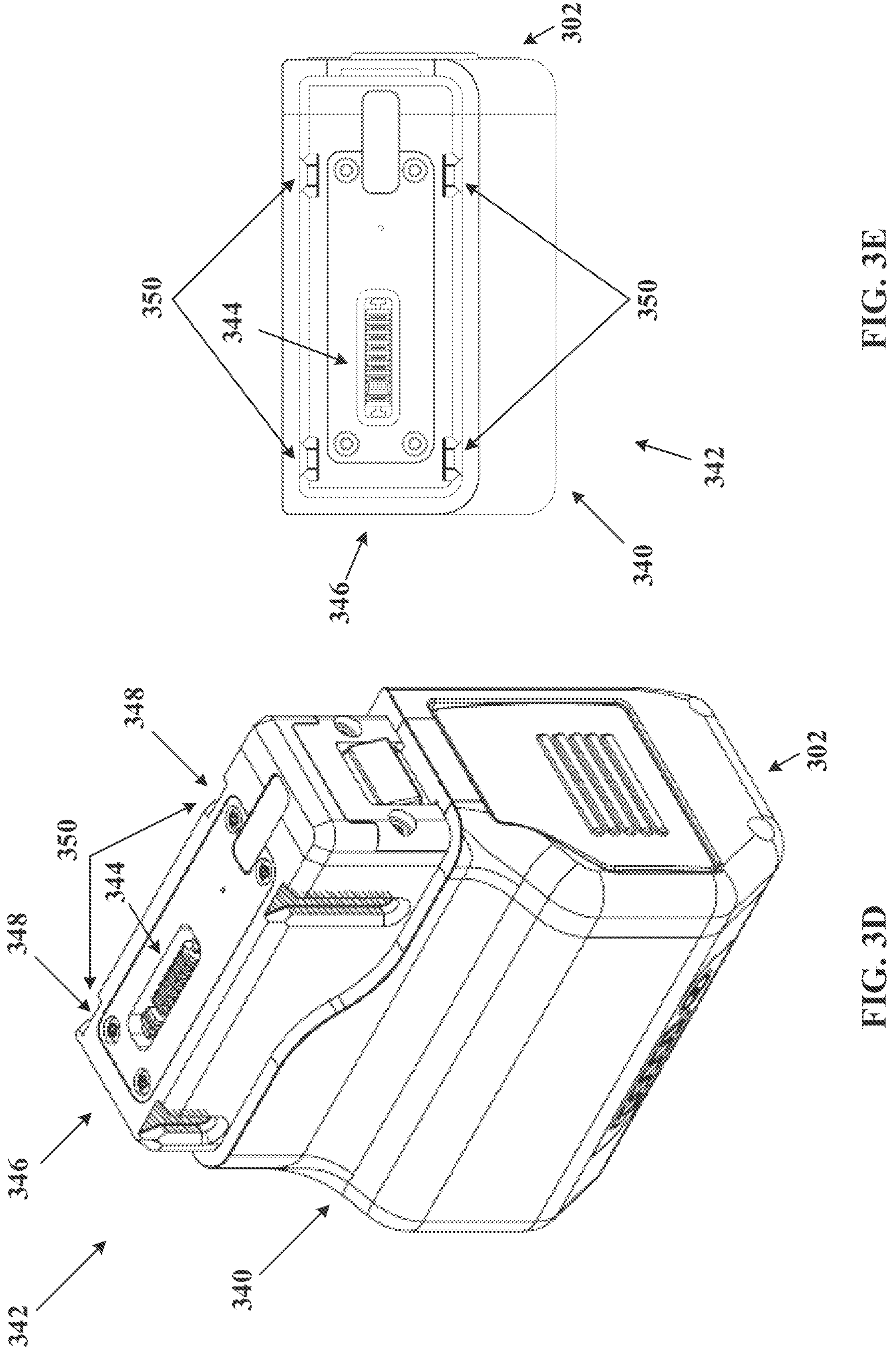

As shown in FIGS. 3D-3E, end cap 302 may be secured to battery housing 340 of battery 342. One or more battery cells (not shown) for powering an implantable heart pump and/or a controller may be housed within battery housing 340 and secured in place by end cap 302. Battery 342 may include one or more electrical contacts 344, in electrical communication with the one or more battery cells, which may be designed to contact one or more corresponding electrical contacts of an associated device or component (e.g., a controller, tethered power adapter, or battery charger) and to thereby supply power to (or receive power from) the associated device or component.

Battery housing 340 (and/or an external controller housing of a controller with which battery 342 may be used; not shown) may include retainer 346 designed to retain battery housing 340 to the external controller housing in an unlocked position (as further described above, for example, with respect to battery housing 204 of FIGS. 2A-2B), by applying a retentive force, to prevent unintended detachment of battery housing 340 from the external controller housing due to the weight of battery 342 or other external factors. The retentive force applied by retainer 346 may be such that a user (e.g., a typical LVAD patient) may be able to detach and remove battery housing 340 from the external controller housing in the unlocked position.

Illustratively, retainer 346 may include one or more friction surfaces 348 located on at least one of battery housing 340 or the external controller housing. For example, as shown in FIGS. 3D-3E, retainer 346 may include one or more friction surfaces 348 integral to battery housing 340 and located about one or more guide channels 350 of battery housing 340. The external controller housing associated with battery housing 340 may, for instance, include one or more guides or rails corresponding to guide channel(s) 350. The guides/rails and/or guide channels 350 may direct battery housing 340 to frictionally engage with the external controller housing at friction surfaces 348 and to thereby direct electrical contacts 344 of battery 342 to engage with corresponding electrical contacts within the external controller housing when battery housing 340 is attached to the external controller housing. As such, retainer 346 may ensure a tight and reliable interface between battery 342 and the controller via which the implantable heart pump may be powered and controlled.

Alternatively, or in addition, retainer 346 may include one or more retention springs (not shown) positioned between the external controller housing and battery housing 340. As another example (not shown), retainer 346 may include one or more magnets connected to the external controller housing and one or more corresponding magnets connected to battery housing 340. The magnet(s) connected to the external controller housing may be designed to magnetically engage with the magnet(s) connected to battery housing 340 and to thereby generate the retentive force.

Figure 3G:
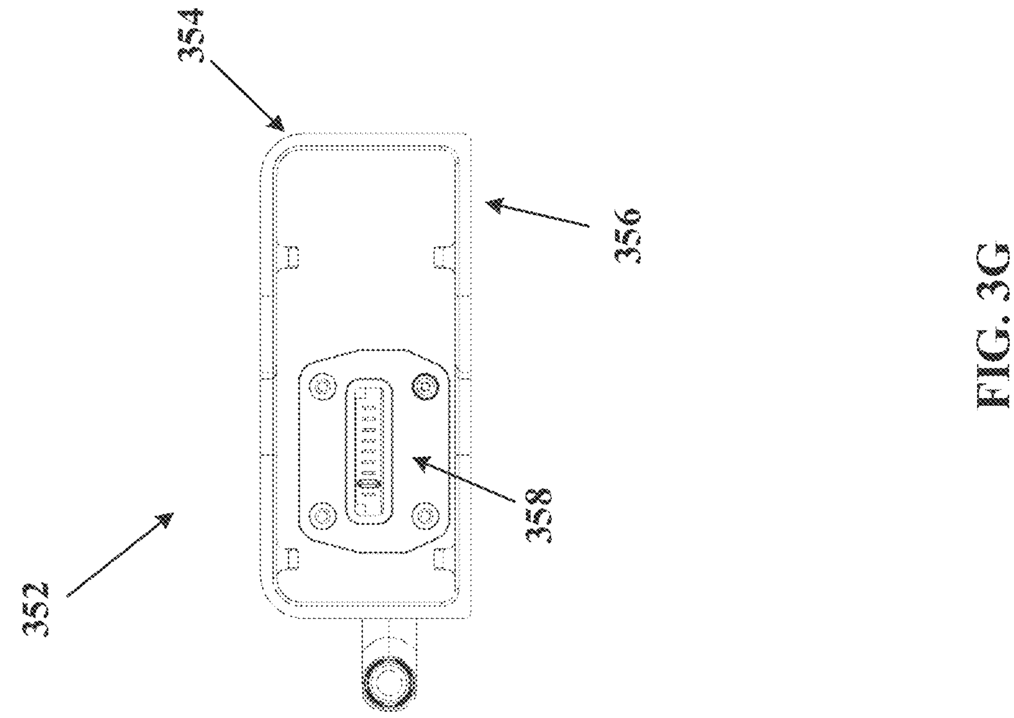
Figure 3F:
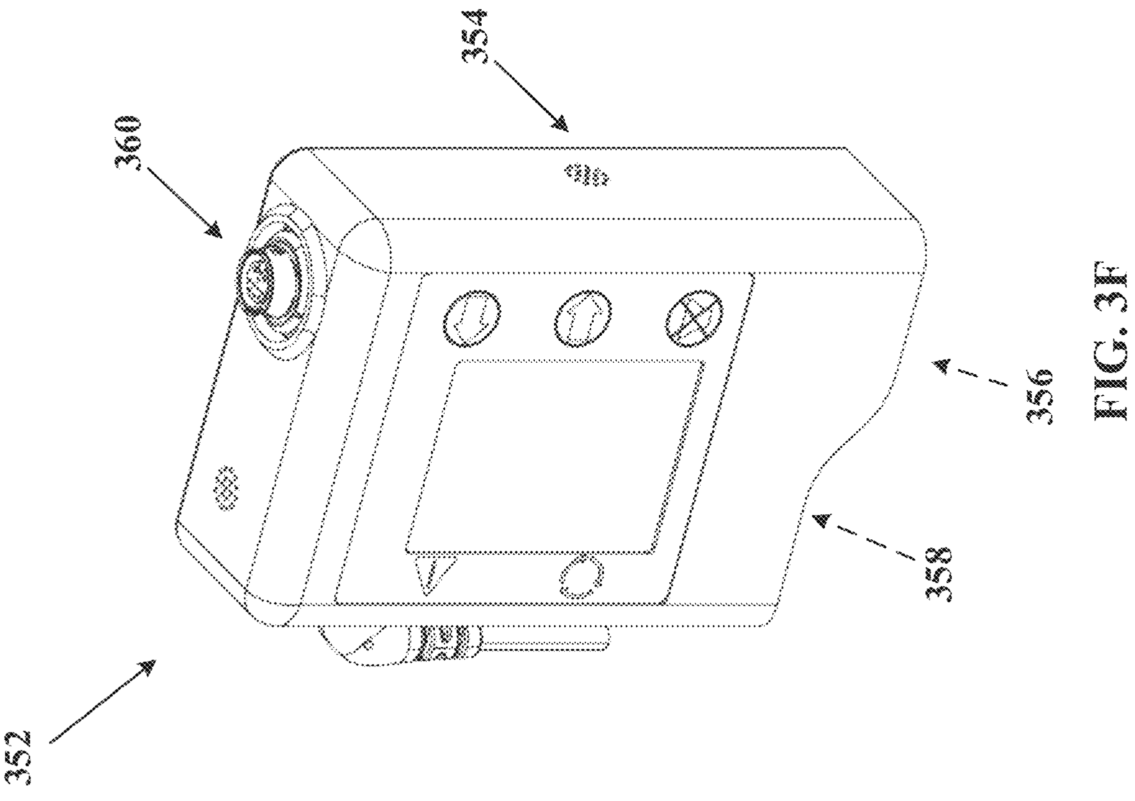

As shown in FIGS. 3F-3G, controller 352 for controlling the implantable heart pump may include external controller housing 354 designed to house a processor (not shown) that may be programmable to control the implantable heart pump. External controller housing 354 may be designed to receive and be removably attached to battery housing 340 such that battery 342 may be connected to controller 352. For example, external controller housing 354 may include latch receiver 356 designed to engage with latch protrusion 310 when battery housing 340 is in a locked position (as further described above, for example, with respect to battery housing 204 of FIGS. 2A-2B) and to thereby lock external controller housing 354 to battery housing 340. Controller 352 may further include one or more electrical contacts 358 corresponding to electrical contacts 344 of battery 342 such that battery 342 may supply power to controller 352 when attached. External controller housing 354 may further include power port 360 designed to receive power from any number of external power supplies. For example, power port 360 may be designed to connect to a connector (not shown). The connector may be connected, via cable, to a tethered power adapter or an external power adapter such that controller 352 may interchangeably receive power from a portable (e.g., battery) or on-grid (e.g., AC wall outlet) source. A cap (not shown) may be attached to external controller housing 354 and may be removably attachable to power port 360 to protect power port 360 from foreign dirt or debris when not in use.

Figure 3H:
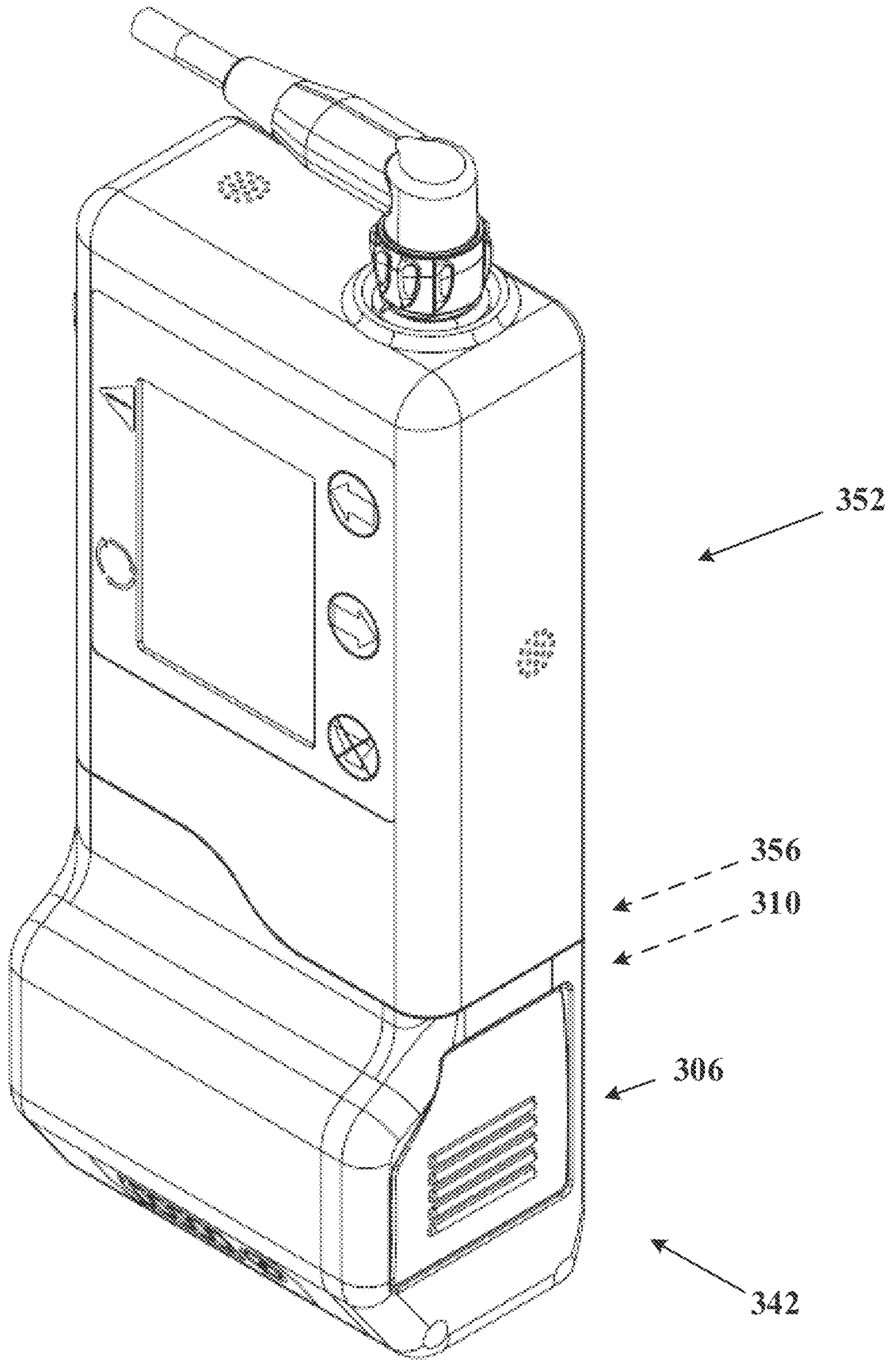
Figures 3I, 3J, 3K, 3L:
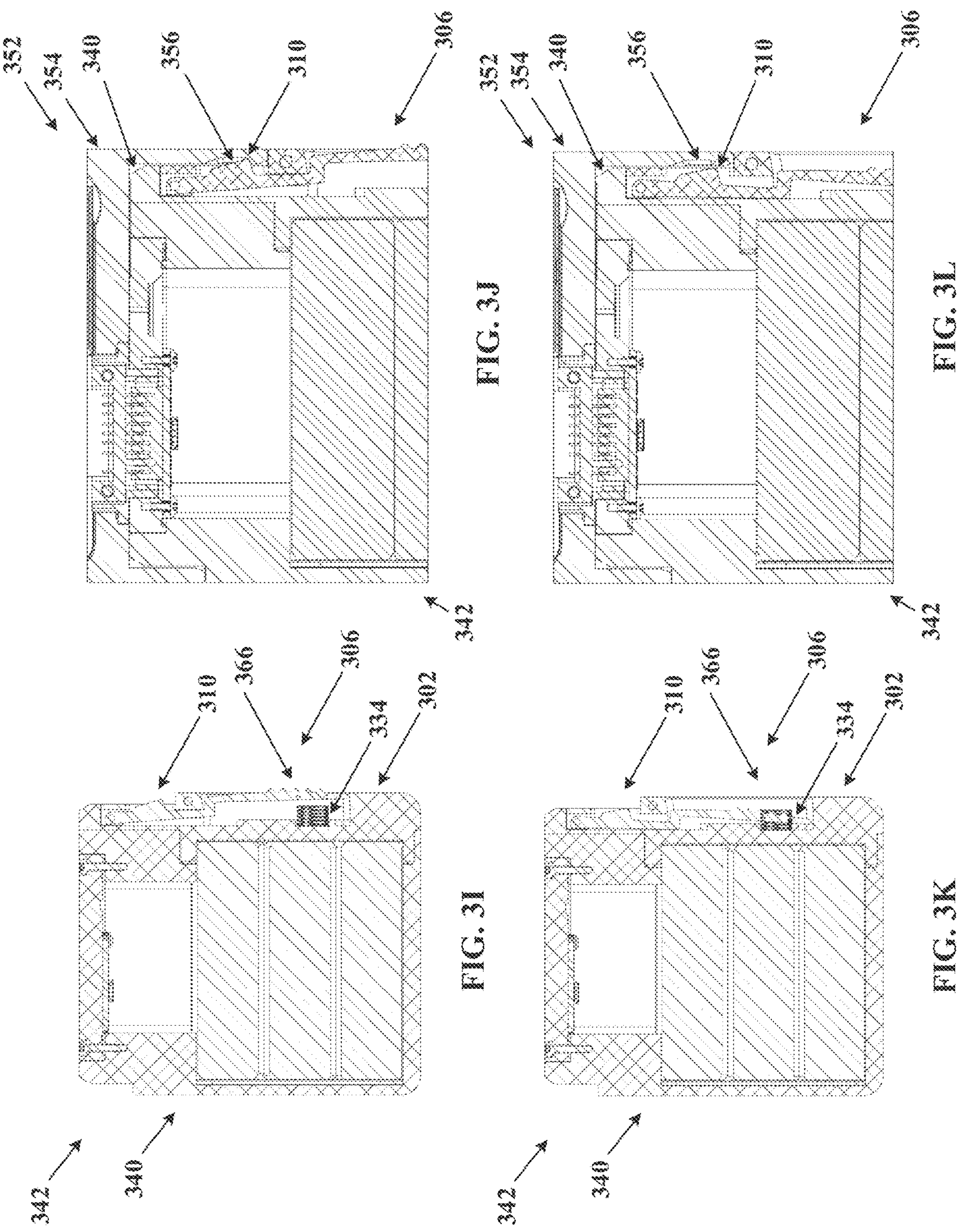

As shown in FIG. 3H, battery 342 may be removably installed in controller 352 to provide power to controller 352 and/or to the implantable heart pump that may be controlled by controller 352. Latch protrusion 310 may be engaged with latch receiver 356 to lock battery 342 in place relative to controller 352. Button 306 may be easily accessible to a user with battery 342 installed in controller 352.

As shown in FIGS. 3I-3L, button 306 and associated components may provide for improved ergonomics over existing components with respect to installation of battery 342 in controller 352 or removal of battery 342 from controller 352, particularly in regards to use by a typical user of an implantable heart pump exhibiting diminished physical capabilities. For example, button 306 may have textured surface 366 to provide a user with a graspable, anti-slip, or tactile surface for holding controller 352 and/or actuating button 306. Spring 332 may be designed to bias button 306 away from end cap 302 by a distance (e.g., 4-5 millimeters) determined to provide a tactile feedback to the user when button 306 is sufficiently depressed to cause latch protrusion 310 to disengage from latch receiver 356. At the same time, the predetermined distance may not be so great as to unduly increase the size of controller 352 and/or battery 342 for purposes of handling or carrying by the user.

Button 306 may be designed to be depressed toward battery housing 340 to cause latch protrusion 310 to disengage from latch receiver 356 by applying a depressive force corresponding to an expected grip strength of the user. Spring 332 may further be selected based on the expected grip strength of the user to ensure that the user, who may have diminished strength (particularly in his or her hands), may still effectively depress button 306. Button 306 may be a single button that must be depressed to permit battery housing 340 to be detached and removed from external controller housing 354. Button 306 may be depressed single-handedly (e.g., by either a thumb or one or more fingers of a user), which may be beneficial for requiring the use of only one hand and thereby allowing the user to depress button 306 with the same hand in which he or she may be holding controller 352. Such single-handed operation of button 306 may leave the user's remaining hand free to perform other tasks such as removing battery 342 from controller 352.

Figures 4A, 4B:
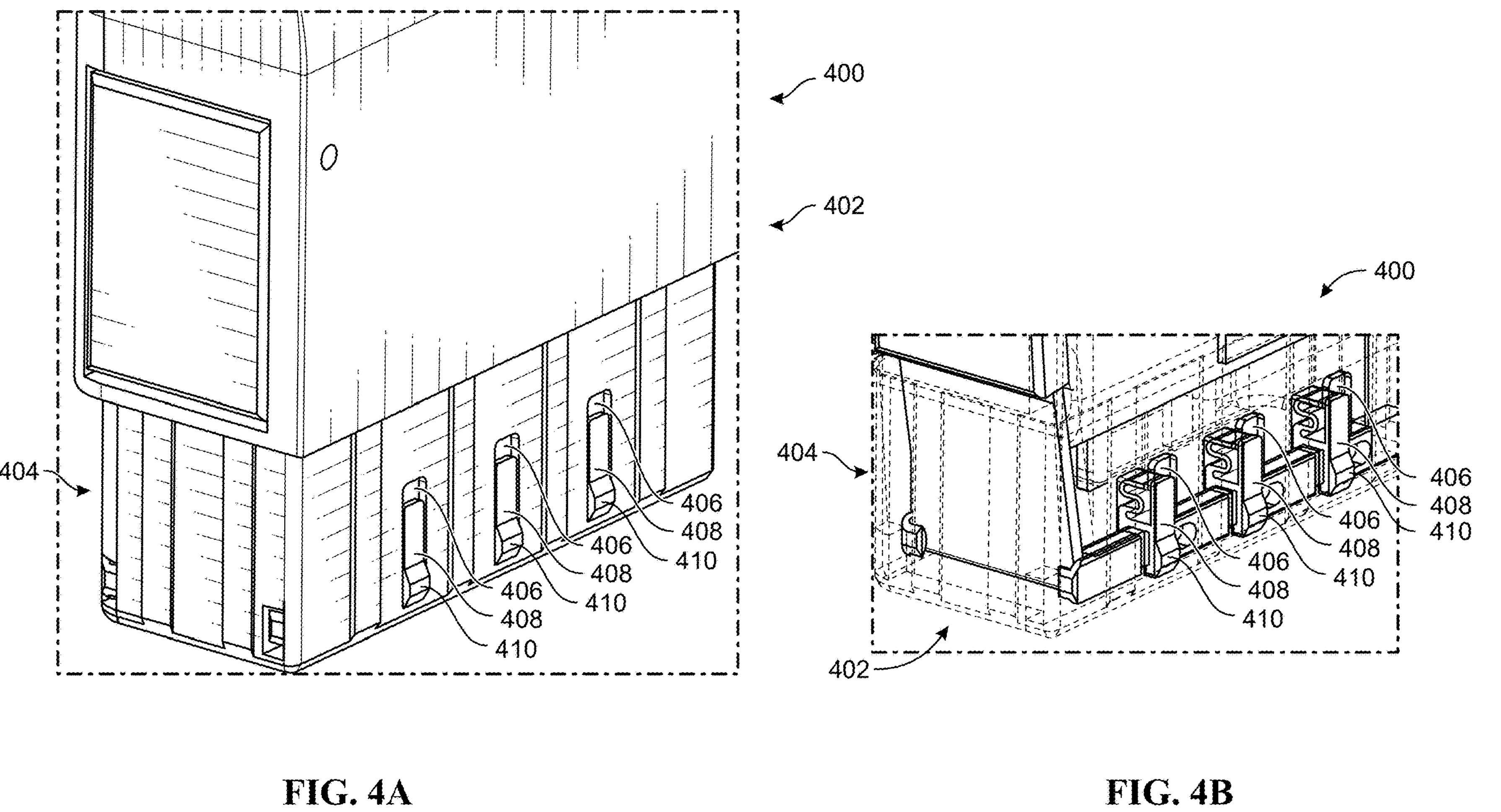
FIGS. 4A-4B are perspective views of an exemplary retainer that may be used with a battery housing.

Referring now to FIGS. 4A-4B, and in brief overview, an alternative retainer for retaining a battery housing to an external controller housing (or to any other housing) is illustrated. As shown in FIGS. 4A-4B, battery 400 may include battery housing 402. Battery housing 402 may include extruded portion 404, which may have one or more recesses 406 designed to receive one or more retention springs 408. Retention springs 408 may be stamped springs formed from spring steel or may be any other types of springs designed for retention purposes. Each retention spring 408 may, for example, include retention portion 410, which may extend outside of battery housing 402 (e.g., beyond an external surface area of extruded portion 404). When battery housing 402 is received, for example, by an external controller housing of a controller (not shown), retention portions 410 of retention springs 408 may engage with and be depressed inwardly by an inside surface of the external controller housing (which may be a relatively smooth surface or may have channels, recesses, or any other surface profile corresponding to retention portions 410). As such, retention portions 410 may be positioned between battery housing 402 and the external controller housing and may thereby apply a retentive force to the inside surface of the external controller housing.

The retentive force may be sufficient to prevent unintended detachment of battery housing 402 from the external controller housing with battery housing 402 in an "unlocked" position (as further described, for example, with respect to battery housing 204 of FIGS. 2A-2B). Still, in the unlocked position, the retentive force provided by retention springs 408 against the inside surface of the external controller housing may be minimal enough that a user may be able to detach and remove battery housing 402 from the external controller housing. For example, with battery housing 402 in the unlocked position, the user may be able to manually pull apart battery housing 402 and the external controller housing despite the retentive force applied by retention springs 408. As will be understood, retention springs 408 may be specifically designed to provide a retentive force that a typical user of an implantable heart pump (e.g., a typical LVAD patient) would be able to overcome.

Figure 5B:
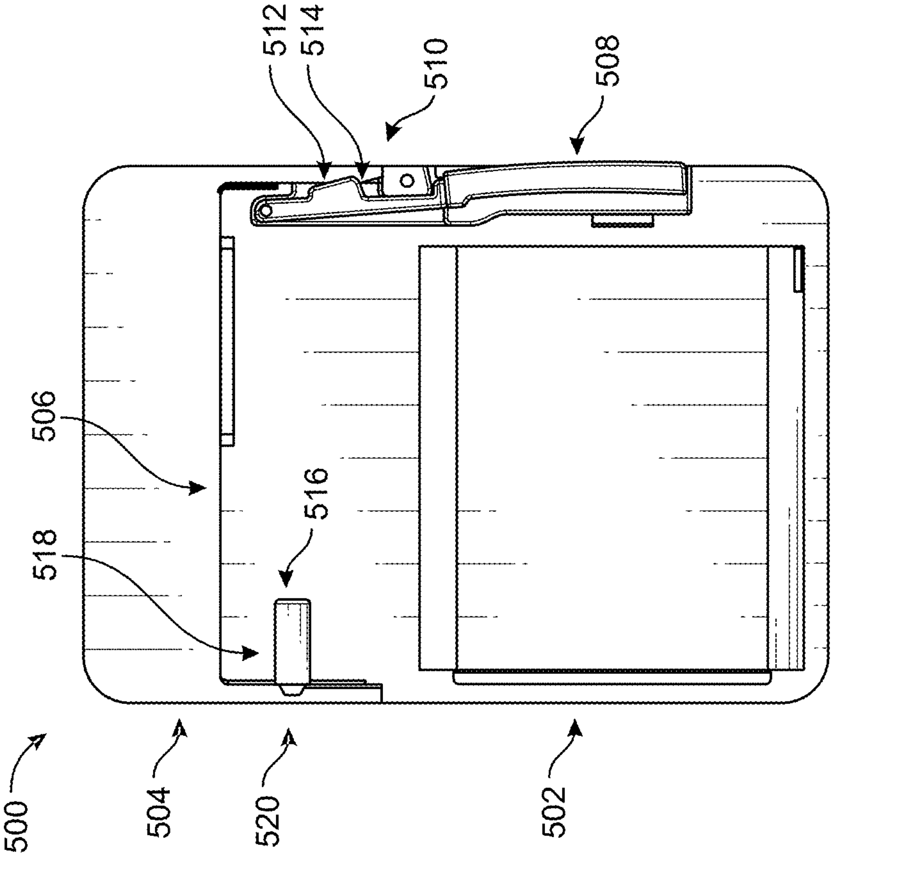
FIGS. 5A-5B are perspective views of another exemplary retainer that may be used with a battery housing and an external housing.
Figure 5A:
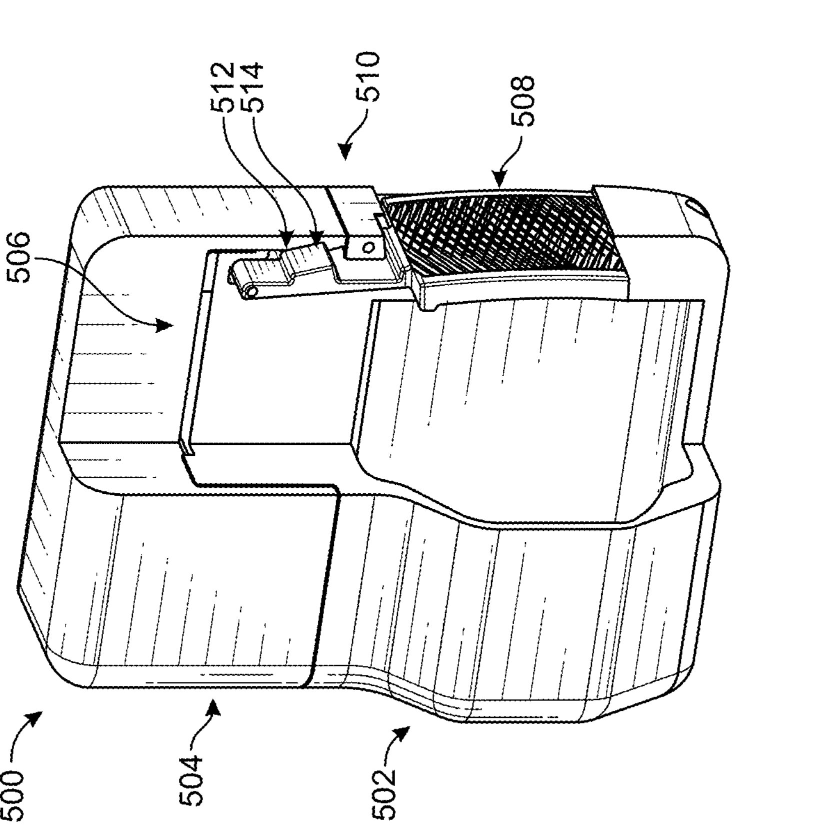
Figures 6A, 6B, 6C, 6D:
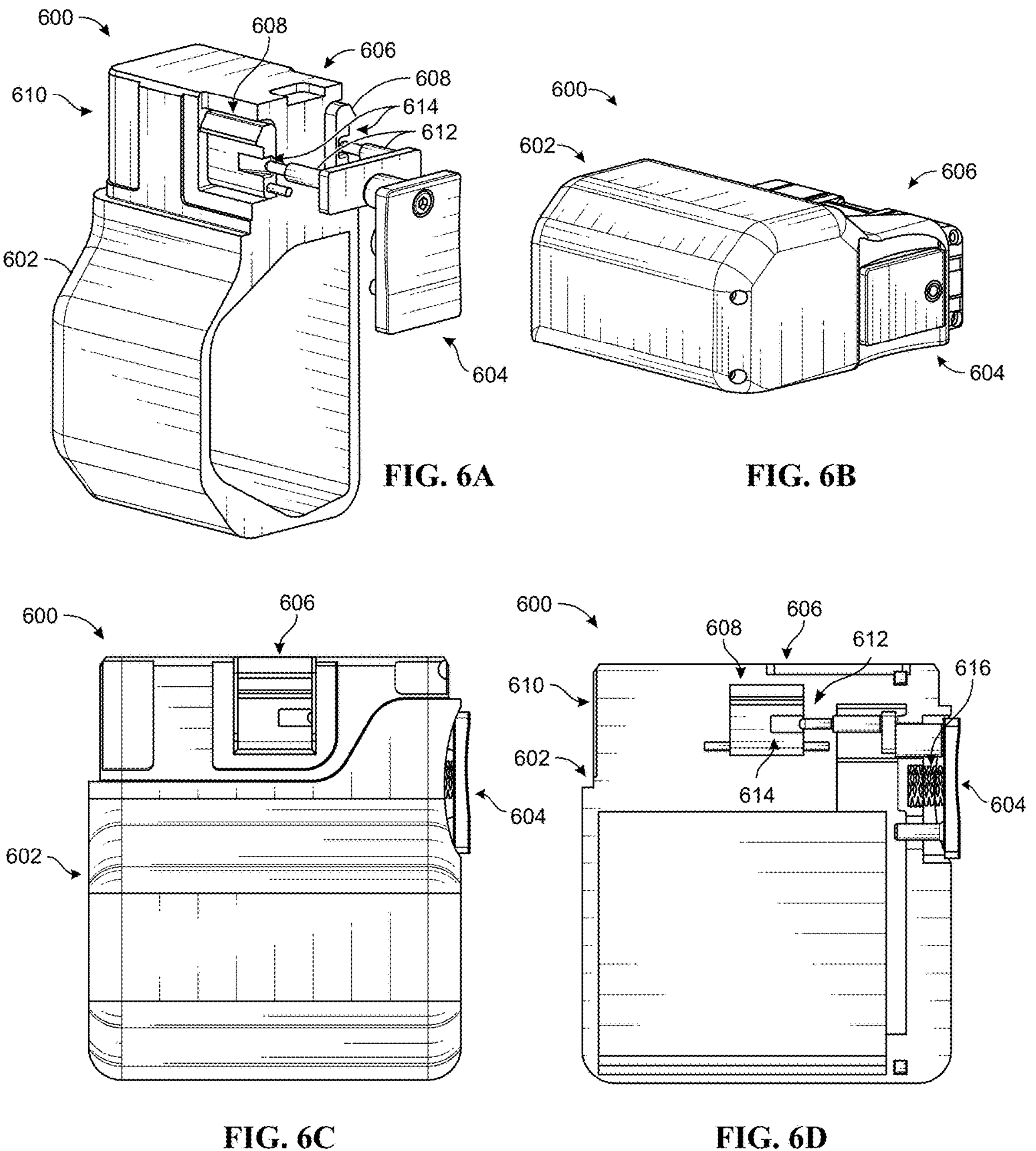
FIGS. 6A-6D are perspective and other views of yet another exemplary retainer that may be used with a battery housing.

Referring now to FIGS. 5A-5B, and in brief overview, another alternative retainer for retaining a battery housing to an external controller housing (or to any other housing) is illustrated. As shown in FIG. 5A, system 500 may include battery housing 502 and/or external housing 504 (which may be, for example, an external controller housing of a controller, a tethered housing of a tethered power adapter, or any other housing designed to receive a battery housing in association with powering or controlling an implantable heart pump). Battery housing 502 may include extruded portion 506 designed to be received by and removably attached to external housing 504. Battery housing 502 may be connected to button 508. Latch 510 may extend from button 508 to latch protrusion 512 along extruded portion 506 of battery housing 502. External housing 504 may include latch receiver 514 corresponding to latch protrusion 512. Battery housing 502 may have "locked" and "unlocked" positions, corresponding to relative positions of button 508, for engaging and disengaging battery housing 502 from external housing 504 (as further described, for example, with respect to battery housing 204 of FIGS. 2A-2B).

As shown in FIG. 5B, extruded portion 506 of battery housing 502 may have cavity 516 to receive retainer 518 (e.g. a ball spring). External housing 504 may have detent 520 corresponding to retainer 518 such that retainer 518 may engage with external housing 504 when battery housing 502 is received within external housing 504. When latch protrusion 512 is engaged with latch receiver 514 in the locked position, retainer 518 may be fixedly engaged with detent 520 to further restrict disengagement of battery housing 502 from external housing 504. When button 508 is depressed toward battery housing 502 by a user and latch protrusion 512 is thereby disengaged from latch receiver 514, the user may be able to apply a force (which may be minimal, for example, to accommodate the physical capabilities of a typical LVAD patient) to disengage retainer 518 from detent 520. However, in the absence of such user-applied force, retainer 518 may apply a retentive force (e.g., a spring force) sufficient to prevent battery housing 502 from unintentionally or unexpectedly detaching from external housing 504. Accordingly, retainer 518 may provide an effective safety mechanism related to battery replacement without unduly increasing weight, maintenance concerns, etc., associated with system 500.

Referring now to FIGS. 6A-6D, and in brief overview, a further alternative retainer for retaining a battery housing to an external controller housing (or to any other external housing) is illustrated. As shown in FIGS. 6A-6D, battery 600 may include battery housing 602 designed to house one or more battery cells to supply power to an implantable heart pump (not shown). Battery housing 602 may be connected to button 604. Button 604 may be designed to be depressed by a user and to thereby cause battery housing 602 to detach and unlock from an external housing (e.g., an external controller housing of a controller for controlling the implantable heart pump; not shown). Retainer 606, which may include one or more clips 608, may be externally located about extruded portion 610 of battery housing 602. One or more extensions 612 may extend from button 604 to be received by one or more corresponding recesses 614 in clips 608 to allow button 604 to be depressed by the user when clips 608 have been installed. Spring 616 may be positioned between button 604 and extruded portion 610 of battery housing 602 to bias button 604 away from battery housing 602 and/or clips 608.

Clips 608 may be designed to removably engage with one or more interior surfaces of the external housing, thereby applying a retentive force to retain the battery housing to the external housing, regardless of whether battery housing 602 may be unlocked from the external housing at a given time, while still providing for the user to manually remove battery housing 602 from the external housing in an unlocked position. The external housing may include one or more friction surfaces (rather than smooth surfaces) to engage with clips 608 when battery housing 602 is received by the external housing. The friction surfaces may, by engaging with clips 608, increase the retentive force that may be applied to retain the battery housing to the external housing.

Figures 7A, 7B, 7C, 7D:
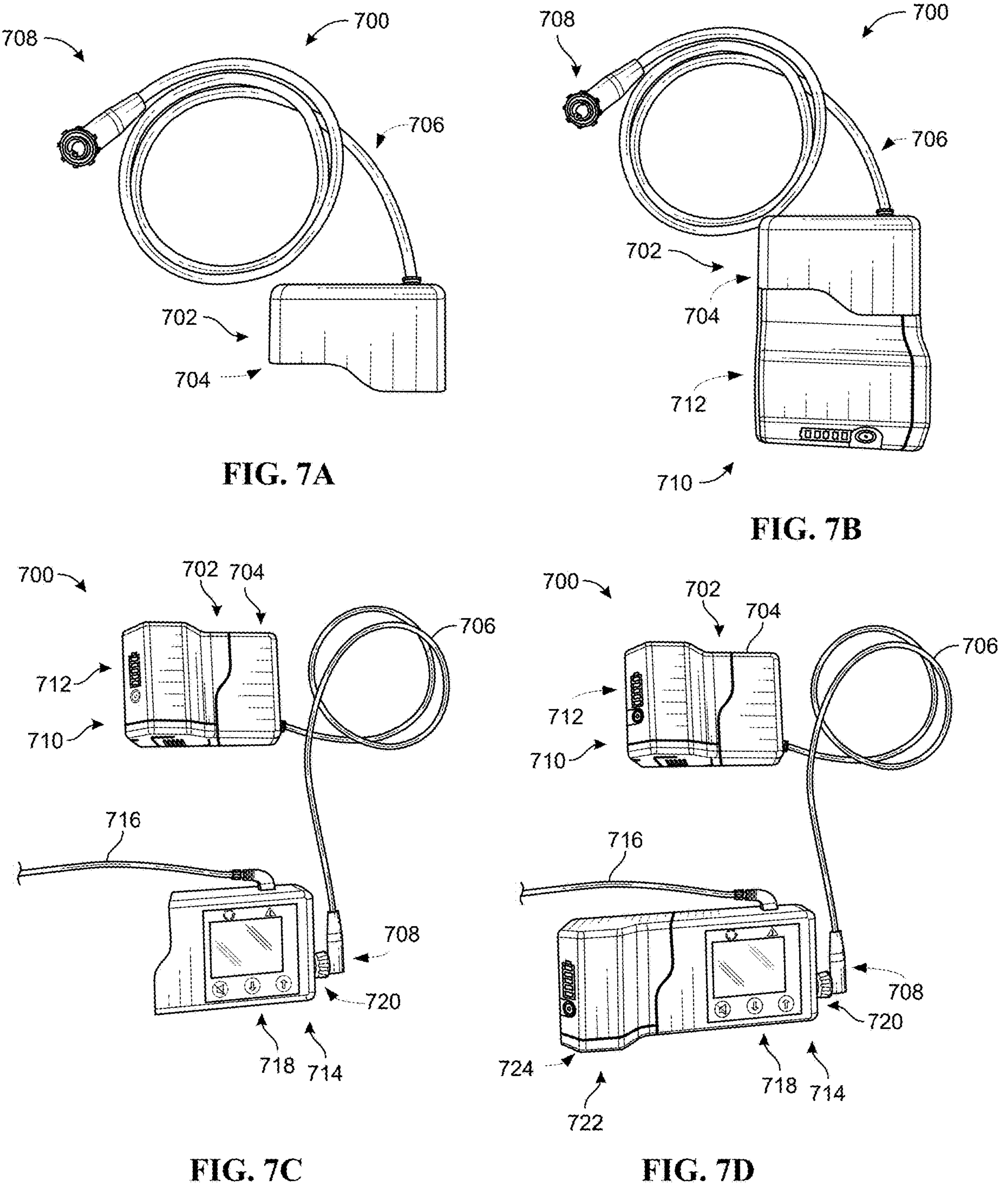
FIGS. 7A-7D are perspective views of an exemplary system for powering and controlling an implantable heart pump, including a tethered power adapter.

Referring now to FIGS. 7A-7D, and in brief overview, a system for powering and controlling an implantable heart pump, the system including a tethered power adapter, is illustrated. As shown in FIG. 7A, system 700 may include tethered power adapter 702. Tethered power adapter 702 may include tethered housing 704. Tethered housing 704 may be connected to one end of tethering cable 706. An opposing end of tethering cable 706 may be connected to connector 708.

As shown in FIG. 7B, system 700 may further include battery 710. Battery 710 may include battery housing 712 designed to house one or more battery cells for supplying power to one or more external devices such as an implantable heart pump and/or associated components (not shown). Battery housing 712 may be received by and removably attached to tethered housing 704. As such, battery 710 may be permitted to supply power to one or more external devices (e.g., the implantable heart pump and/or an associated controller) via tethering cable 706. As will be understood and further explained throughout the present disclosure, power supplied by battery 710 when connected to tethered power adapter 702 may be primary, tethered, supplemental, or backup in nature.

As shown in FIG. 7C, system 700 may further include controller 714. Controller 714 may be designed to control and/or supply power to the implantable heart pump via cable 716 and may include external controller housing 718 with power port 720 to connect to and receive power from any number of external power supplies. For example, connector 708 associated with tethered power adapter 702 may be designed to be connected to power port 720 such that battery 710 connected to tethered power adapter 702 may supply power to controller 714 and/or the implantable heart pump via tethering cable 706. Alternatively, a different connector (not shown) having a similar interface to that of connector 708 may be connected to an external power adapter (not shown) designed to supply power from an external power supply (e.g., a hardwired or AC power source provided, for instance, via a wall outlet) to controller 714 and/or the implantable heart pump. Accordingly, controller 714 may receive power via power port 720 from a range of external sources, in addition to or instead of any local power sources (e.g., batteries) integral or directly connected to controller 714.

As shown in FIG. 7D, system 700 may further include battery 722. Battery 722 may include battery housing 724 designed to house one or more battery cells for supplying power to the implantable heart pump and/or controller 714. Battery housing 724 may be received by and removably attached to external controller housing 718. As such, battery 722 may be permitted to supply power directly to controller 714 and/or to the implantable heart pump via cable 716. As with power supplied by battery 710, power supplied by battery 722 may be primary, tethered, supplemental, or backup in nature depending on the availability of any additional power sources (or lack thereof). Controller 714 may include, alternatively or in addition to any other power source, an integral battery (not shown). The integral battery may be used, for example, to supply power to controller 714 and/or the implantable heart pump in circumstances where no other power source is available (e.g., as an emergency reserve battery).

System 700 may provide numerous combinations for supplying power to controller 714 and/or the implantable heart pump, which may offer improved flexibility over existing power-supply systems associated with implantable heart pumps such as LVADs. As one example, batteries 710 and 722 may be used interchangeably, which may be more cost-effective and/or provide for greater flexibility in powering controller 714 and/or the implantable heart pump via local or tethered connection. For instance, battery housing 724 of battery 722 and battery housing 712 of battery 710 may have similar interfaces such that battery 722 or battery 710 may be received interchangeably by external controller housing 718 of controller 714 and tethered housing 704 of tethered power adapter 702. Accordingly, either battery 710 or battery 722 may be used to provide local power when directly connected to controller 714 or tethered power when connected to tethered power adapter 702. As another example, because power port 720 of controller 714 may be interchangeably connectable to connector 708 associated with tethered power adapter 702 or any number of other connectors associated with various external power adapters, a user may optionally select whether to use power port 720 to receive grid-connected power from an external power supply (e.g., via an external power adapter connected to a wall outlet) or to receive power from a portable power supply (e.g., via tethered power adapter 702 connected to battery 710). Further example setups for powering implantable heart pumps and/or associated controllers (as well as associated benefits in the context of typical use cases for implantable heart pumps, e.g., use by typical LVAD patients) are provided throughout the present disclosure, for instance, with respect to FIGS. 1A-1B, or will otherwise be understood.

Figure 8:
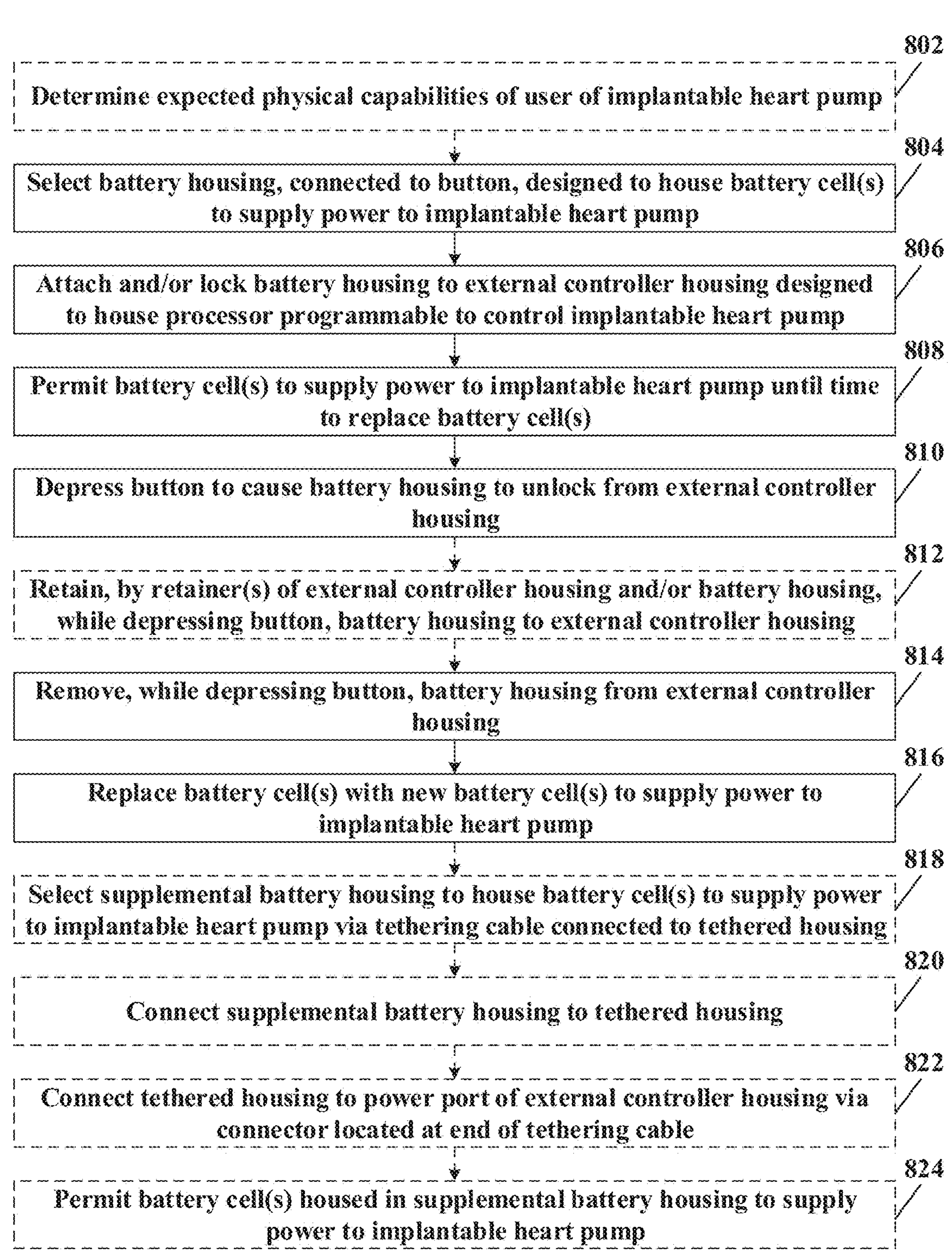
FIG. 8 is a flowchart illustrating example steps for powering and controlling an implantable heart pump.

Referring now to FIG. 8, and in brief overview, process 800 illustrates example steps for powering and controlling an implantable heart pump. It will be understood that the various systems, devices, or components described in relation process 800 may be the same as (or similar to) any corresponding systems, devices, or components described herein in relation to any of the preceding figures or may be different systems, devices, or components.

As shown in FIG. 8, at step 802, one or more expected physical capabilities of a user of an implantable heart pump may be determined. For example, the user of the implantable heart pump may be a typical LVAD patient and/or may have diminished physical capabilities (e.g., grip strength, dexterity, sensory sensitivity, or mobility) due to health complications. In view of the expected physical capabilities of the user, one or more components or devices used in powering and/or controlling the implantable heart pump may be designed or otherwise selected to optimize ergonomics and usability for the user (as further described below).

At step 804, a battery housing of a battery may be selected. The battery housing may be designed to house one or more battery cells to supply power to the implantable heart pump. A button may be connected to the battery housing. A latch may extend from the button to a latch protrusion. At step 806, the battery housing may be attached to an external controller housing of a controller such that the latch protrusion engages a latch receiver of the external controller housing to thereby lock the battery housing to the controller housing. The external controller housing may be designed to house a processor that is programmable to control the implantable heart pump. At step 808, the battery cell(s) housed in the battery housing may be permitted, via the controller, to supply power to the implantable heart pump until a time to replace the battery cell(s).

At step 810, the button may be depressed toward the battery housing to cause the latch protrusion to disengage from the latch receiver, thereby unlocking the battery housing from the external controller housing. At least one of the external controller housing or the battery housing may include a retainer. The retainer(s) may include, for example, one or more retention springs (e.g., stamped springs or ball springs) positioned between the external controller housing and the battery housing, one or more friction clips or surfaces located on at least one of the external controller housing or the battery housing, or one or more magnets attached to the external controller housing and designed to magnetically engage with one or more corresponding magnets attached to the battery housing. At step 812, the retainer may, while the button is being depressed, retain the battery housing to the external controller housing to thereby prevent unintended detachment of the battery housing from the external controller housing in an unlocked position. At step 814, the battery housing may be removed from the external controller housing while the button is being depressed. At step 816, the battery cell(s) may be replaced with a new set of battery cell(s) for connecting to the external controller housing for supplying power to the implantable heart pump.

As noted above, the expected physical capabilities of the user of the implantable heart pump may factor into the design or selection of various components associated with powering or controlling the implantable heart pump in order to optimize usability. For example, an expected grip strength of a user and/or other hand function(s) of the user may be determined, which may inform setup of the latch, button, and associated components used to lock or unlock the battery housing from the external controller housing. In some embodiments, for instance, a spring may be positioned between the button and the battery housing. The spring may be selected to bias the button away from the battery housing by a distance determined to provide a tactile feedback to the user when the button is sufficiently depressed to cause the latch protrusion to disengage from the latch receiver. Depressing the button toward the battery housing to cause the latch protrusion to disengage from the latch receiver may include applying a depressive force corresponding to the expected grip strength of the user. Alternatively, or in addition, the button may be a single button designed to cause the latch protrusion to disengage from the latch receiver. The button may be designed to be depressed by either a thumb or one or more fingers of the user, which may provide for the button to be depressed in a single-handed manner by the user.

The external controller housing may further include a user interface designed to provide information on the implantable heart pump (e.g., performance metrics, operational settings, or battery life) to the user. The external controller may further be designed to house a battery (e.g., an emergency reserve battery) to supply power to the implantable heart pump. The battery housed in the controller may be permitted to supply power to the controller and/or the implantable heart pump when the battery cell(s) housed in the battery housing are not supplying power to the implantable heart pump (e.g., due to lack of charge, disconnection, or malfunction).

In order for the user to use the implantable heart pump, a percutaneous cable may be connected to the external controller housing and to the implantable heart pump. The percutaneous cable may be designed to extend through skin of the user. Accordingly, the implantable heart pump may be designed to be implanted in the user, controlled by an extracorporeal controller (e.g., the controller associated with the external controller housing described herein), and/or powered by one or more extracorporeal sources of power (e.g., the battery cell(s) associated with the battery housing or battery integral to the controller described herein or another source of portable or grid-supplied power). The implantable heart pump may thereby be powered and/or controlled in a manner conducive to the particular logistical requirements of the user (e.g., mobility needs, "excursion" time, or availability of a long-term static power source).

At step 818, for example, a supplemental battery housing may be selected. The supplemental battery housing may be designed to house one or more supplemental battery cells to supply power to the implantable heart pump via a tethering cable connected to a tethered housing of a tethered power adapter at one end of the tethering cable. At step 820, the supplemental battery housing may be attached to the tethered housing. As will be understood, the supplemental battery housing may have a similar interface to that of the battery housing described above. Accordingly, either may be interchangeably attached to the tethered housing or the external controller housing depending, for instance, on the respective charge levels of the battery cell(s) and the supplemental battery cell(s) and/or the particular needs or preferences of the user. At step 822, the tethered housing may be connected to a power port of the external controller housing via a connector located at another end of the tethering cable. At step 824, the supplemental battery cell(s) may be permitted to supply power to the implantable heart pump via the tethered power adapter and the controller.

The power port of the external controller housing may be designed to interchangeably receive power from the supplemental battery cell(s) via the tethering cable or from an external power supply (e.g., grid-supplied power via an AC wall outlet and an external power adapter). For example, the connector associated with the tethering cable may have a similar interface to any number of other connectors associated with various external power supplies, all of which may be easily interchanged. As such, the user of the implantable heart pump may benefit from a robust range of options and combinations for supplying power to the implantable heart pump and connected components. Associated benefits may include, for instance, increased mobility due to longer potential "excursion" time on battery power and/or improved reliability of continued power supply due to built-in power redundancies or backup options between grid-supplied power, primary battery power, and/or tethered, supplemental, or reserve battery power.

Although specific embodiments of the present disclosure have been described herein, one of ordinary skill in the art will recognize that numerous other modifications and alternative embodiments are within the scope of the disclosure. For example, any functionality described with respect to a particular device or component may be performed by any other device or component. Further, while various illustrative implementations have been described in accordance with embodiments of the disclosure, one of ordinary skill in the art will appreciate that numerous other modifications to the illustrative implementations described herein are also within the scope of the disclosure.

Certain aspects of the disclosure are described above with reference to block and/or flow diagrams of systems, methods, and apparatuses according to example embodiments. It will be understood that one or more blocks of any block and/or flow diagram, and combination(s) of blocks in the block and/or flow diagrams, respectively, may not necessarily need to be performed in the order presented or may not necessarily need to be performed at all, according to some embodiments. Further, additional components and/or operations beyond those depicted in blocks of any block and/or flow diagram may be present in certain embodiments.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, amongst other language, “can,” “could,” “might,” or “may,” unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily require deciding whether these features, elements, and/or steps are included or are to be performed in any particular embodiment.

What is claimed is:

1. A system for powering and controlling an implantable heart pump, the system comprising:

an external controller housing configured to house a processor, the processor configured to be programmed to control the implantable heart pump, the external controller housing comprising a latch receiver and having a first asymmetric shape extending entirely around the external controller housing with respect to a primary longitudinal axis of the external controller housing and defining a void;

a battery housing configured to be removably coupled to the external controller housing, the battery housing configured to house a plurality of battery cells to supply power to the implantable heart pump, the battery housing having an outer region defining a second asymmetric shape extending entirely around the battery housing with respect to a primary longitudinal axis of the battery housing and a protruding portion;

a button coupled to the battery housing, the button configured to be biased away from the battery housing in a locked position; and a latch extending from the button to a latch protrusion, wherein, in the locked position, the latch protrusion engages with the latch receiver to lock the external controller housing to the battery housing, wherein the button is configured to be depressed toward the battery housing to cause the latch protrusion to disengage from the latch receiver to permit the battery housing to be decoupled and removed from the external controller housing, and wherein the first asymmetric shape of the external controller housing is configured to interface with the second asymmetric shape of the battery housing such that the first asymmetric shape and the second asymmetric shape conform to one another in a manner that aligns the protruding portion of the battery housing with the void of the external controller housing when the battery housing is coupled to external controller housing.

2. The system of claim 1, further comprising a spring positioned between the button and the battery housing, the spring configured to bias the button away from the battery housing by a distance determined to provide a tactile feedback to a user of the implantable heart pump when the button is sufficiently depressed to cause the latch protrusion to disengage from the latch receiver.

3. The system of claim 1, wherein the button is further configured to be depressed toward the battery housing to cause the latch protrusion to disengage from the latch receiver by applying a depressive force corresponding to an expected grip strength of a user of the implantable heart pump.

4. The system of claim 1, wherein the button is a single button configured to permit the battery housing to be decoupled and removed from the external controller housing when the single button is depressed toward the battery housing, the button further configured to be depressed single-handedly by either a thumb or one or more fingers of a user.

5. The system of claim 1, wherein at least one of the external controller housing or the battery housing comprises a retainer, the retainer configured to retain the battery housing to the external controller housing in an unlocked position, by applying a retentive force, to prevent unintended decoupling of the battery housing from the external controller housing, the retainer further configured to permit a user to decouple and remove the battery housing from the external controller housing in the unlocked position.

6. The system of claim 5, wherein the retainer comprises:

one or more retention springs positioned between the external controller housing and the battery housing, one or more friction surfaces disposed on at least one of the external controller housing or the battery housing, or one or more first magnets coupled to the external controller housing and one or more second magnets coupled to the battery housing, the one or more first magnets configured to magnetically engage with the one or more second magnets.

7. The system of claim 6, wherein the retainer comprises the one or more friction surfaces, at least one of the external controller housing or the battery housing comprising one or more guides to direct the battery housing to frictionally engage with the external controller housing at the one or more friction surfaces and to thereby direct one or more first electrical contacts of the plurality of battery cells to engage with one or more second electrical contacts disposed within the external controller housing when the battery housing is coupled to the external controller housing.

8. The system of claim 1, wherein the external controller housing is further configured to house a battery configured to supply power to the implantable heart pump when the plurality of battery cells in the battery housing are not supplying power to the implantable heart pump.

9. The system of claim 1, further comprising a tethered housing configured to receive a supplemental battery housing and to be removably coupled to the external controller housing via a tethering cable, the supplemental battery housing configured to house a plurality of supplemental battery cells to supply power to the implantable heart pump via the tethering cable.

10. The system of claim 9, wherein the tethering cable is coupled to the tethered housing at a first end and comprises a connector configured to be removably coupled to a power port of the external controller housing at a second end, the power port configured to interchangeably receive power from the plurality of supplemental battery cells via the tethering cable or from an external power supply, the implantable heart pump configured to thereby receive power from the plurality of supplemental battery cells or the external power supply, either alone or in combination with the plurality of battery cells.

11. The system of claim 9, wherein the battery housing is further configured to be removably coupled to the tethered housing and the supplemental battery housing is further configured to be removably coupled to the external controller housing.

12. The system of claim 1, wherein the external controller housing comprises a user interface configured to provide information on the implantable heart pump to a user.

13. The system of claim 1, wherein the system comprises the implantable heart pump.

14. The system of claim 1, further comprising a percutaneous cable configured to be coupled to the external controller housing, to extend through skin of a user, and to be coupled to the implantable heart pump.

15. A method for powering and controlling an implantable heart pump, the method comprising:

selecting a battery housing configured to house a plurality of battery cells to supply power to the implantable heart pump, the battery housing having an outer region defining a first asymmetric shape extending entirely around the battery housing with respect to a primary longitudinal axis of the battery housing and a protruding portion, wherein a button is coupled to the battery housing and a latch extends from the button to a latch protrusion;

coupling the battery housing to an external controller housing such that the latch protrusion engages a latch receiver of the external controller housing to thereby lock the battery housing to the external controller housing, the external controller housing having an outer region defining a second asymmetric shape extending entirely around the external controller housing with respect to a primary longitudinal axis of the external controller housing and defining a void, the external controller housing configured to house a processor configured to be programmed to control the implantable heart pump;

permitting the plurality of battery cells to supply power to the implantable heart pump until a time to replace the plurality of battery cells;

depressing the button toward the battery housing to cause the latch protrusion to disengage from the latch receiver;

removing, while depressing the button, the battery housing from the external controller housing; and replacing the plurality of battery cells with a new set of battery cells for coupling to the external controller housing for supplying power to the implantable heart pump, wherein the second asymmetric shape of the external controller housing is configured to interface with the first asymmetric shape of the battery housing such that the first asymmetric shape and the second asymmetric shape conform to one another in a manner that aligns the protruding portion of the battery housing with the void of the external controller housing when the battery housing is coupled to external controller housing.

16. The method of claim 15, wherein the external controller housing is further configured to house a battery to supply power to the implantable heart pump and further comprises a user interface configured to provide information on the implantable heart pump to a user, the method further comprising:

permitting the battery to supply power to the implantable heart pump when the plurality of battery cells are not supplying power to the implantable heart pump; and coupling a percutaneous cable to the external controller housing and to the implantable heart pump, the percutaneous cable configured to extend through skin of the user.

17. The method of claim 15, further comprising:

determining an expected grip strength of a user; and positioning a spring between the button and the battery housing, the spring selected to bias the button away from the battery housing by a distance determined to provide a tactile feedback to the user when the button is sufficiently depressed to cause the latch protrusion to disengage from the latch receiver, wherein depressing the button toward the battery housing to cause the latch protrusion to disengage from the latch receiver comprises applying a depressive force corresponding to the expected grip strength of the user.

18. The method of claim 15, wherein the button is configured to be depressed by either a thumb or one or more fingers of a user, the button being a single button configured to cause the latch protrusion to disengage from the latch receiver.

19. The method of claim 15, wherein at least one of the external controller housing or the battery housing comprises a retainer, the method further comprising:

retaining, by the retainer, while depressing the button, the battery housing to the external controller housing to prevent unintended decoupling of the battery housing from the external controller housing, the retainer comprising:

one or more retention springs positioned between the external controller housing and the battery housing, one or more friction surfaces disposed on at least one of the external controller housing or the battery housing, or one or more first magnets coupled to the external controller housing and one or more second magnets coupled to the battery housing, the one or more first magnets configured to magnetically engage with the one or more second magnets.

20. The method of claim 15, further comprising:

selecting a supplemental battery housing configured to house a plurality of supplemental battery cells to supply power to the implantable heart pump via a tethering cable coupled to a tethered housing at a first end of the tethering cable;

coupling the supplemental battery housing to the tethered housing;

coupling the tethered housing to a power port of the external controller housing via a connector located at a second end of the tethering cable; and permitting the plurality of supplemental battery cells to supply power to the implantable heart pump, wherein the power port is configured to interchangeably receive power from the plurality of supplemental battery cells via the tethering cable or from an external power supply.

* * * * *